United States Patent
Sato

(10) Patent No.: US 12,257,108 B2
(45) Date of Patent: Mar. 25, 2025

(54) ULTRASONIC DIAGNOSTIC APPARATUS AND IMAGE PROCESSING APPARATUS

(71) Applicant: CANON MEDICAL SYSTEMS CORPORATION, Tochigi (JP)

(72) Inventor: Takeshi Sato, Nasushiobara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 109 days.

(21) Appl. No.: 18/161,114

(22) Filed: Jan. 30, 2023

(65) Prior Publication Data

US 2023/0240658 A1 Aug. 3, 2023

(30) Foreign Application Priority Data

Jan. 31, 2022 (JP) ................. 2022-012638

(51) Int. Cl.
*A61B 8/08* (2006.01)
*A61B 8/00* (2006.01)
*A61B 8/06* (2006.01)
*G06T 7/20* (2017.01)

(52) U.S. Cl.
CPC .............. *A61B 8/488* (2013.01); *A61B 8/06* (2013.01); *G06T 7/20* (2013.01); *G06T 2207/10132* (2013.01); *G06T 2207/30104* (2013.01)

(58) Field of Classification Search
None
See application file for complete search history.

(56) References Cited

U.S. PATENT DOCUMENTS

| 7,713,198 B2 | 5/2010 | Sato |
| 10,603,014 B2 | 3/2020 | Sato |
| 2005/0148875 A1 | 7/2005 | Sato |

(Continued)

FOREIGN PATENT DOCUMENTS

| JP | 2005-176997 A | 7/2005 |
| JP | 2016-2379 A | 1/2016 |

OTHER PUBLICATIONS

Bercoff et al., "Ultrafast Compound Doppler Imaging: Providing Full Blood Flow Characterization", IEEE Transactions on Ultrasonics, Ferroelectrics, and Frequency Control, vol. 58, No. 1, 2011, 14 pages.

*Primary Examiner* — Baisakhi Roy
(74) *Attorney, Agent, or Firm* — Oblon, McClelland, Maier & Neustadt, L.L.P.

(57) ABSTRACT

An ultrasonic diagnostic apparatus of an embodiment includes an ultrasonic probe and processing circuitry. The ultrasonic probe repeatedly performs scanning in which a plane wave or a diffused wave is continuously transmitted a plurality of times in the same direction in a plurality of directions. The processing circuitry performs processing of applying a moving target indicator (MTI) filter to an unequal interval data sequence in the same direction obtained by the scanning and extracting a blood flow signal in each of the plurality of directions, performs processing of generating an autocorrelation signal by performing an autocorrelation operation on a plurality of blood flow signals in the same direction for each of the directions, and estimates a velocity value of blood flow on the basis of a complex signal generated by performing complex addition of a plurality of autocorrelation signals generated for the plurality of directions.

5 Claims, 19 Drawing Sheets

(56) References Cited

U.S. PATENT DOCUMENTS

| | | | |
|---|---|---|---|
| 2007/0239015 A1* | 10/2007 | Sato | G01S 15/8979 |
| | | | 600/455 |
| 2015/0080730 A1* | 3/2015 | Kanayama | G06T 7/0012 |
| | | | 600/447 |
| 2015/0327840 A1* | 11/2015 | Hirama | A61B 8/463 |
| | | | 600/443 |
| 2015/0366540 A1 | 12/2015 | Sato | |
| 2016/0089115 A1* | 3/2016 | Sato | A61B 8/06 |
| | | | 600/447 |
| 2017/0252012 A1* | 9/2017 | Nagai | G01S 15/8915 |
| 2017/0340309 A1* | 11/2017 | Ogasawara | A61B 8/0891 |
| 2019/0150897 A1* | 5/2019 | Susumu | A61B 8/5276 |

* cited by examiner

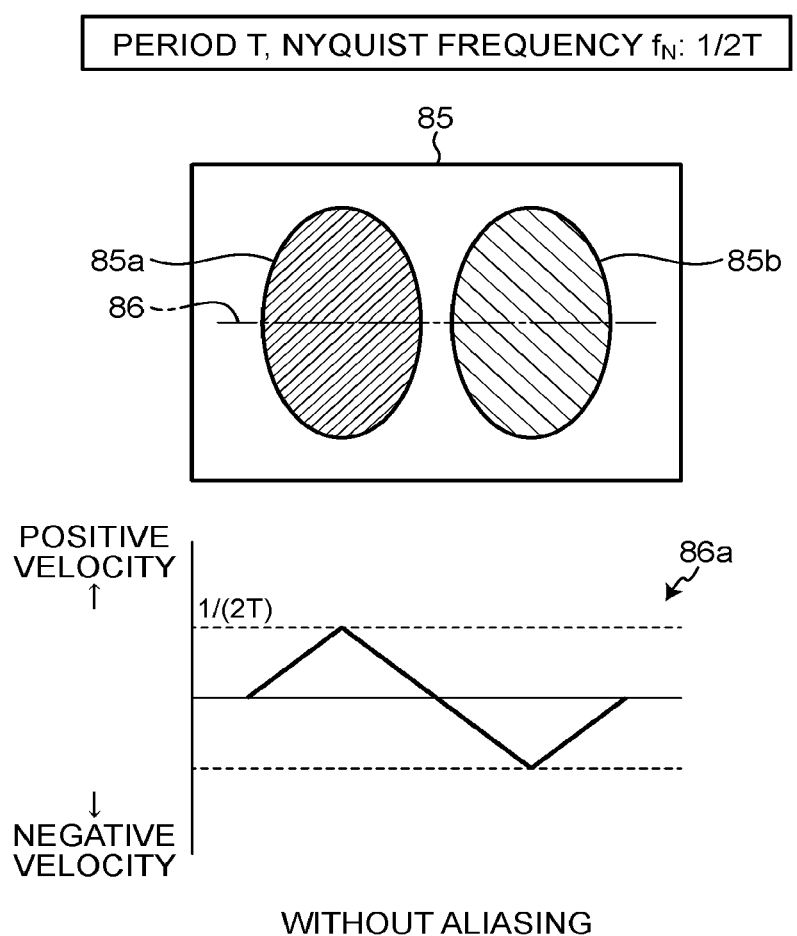

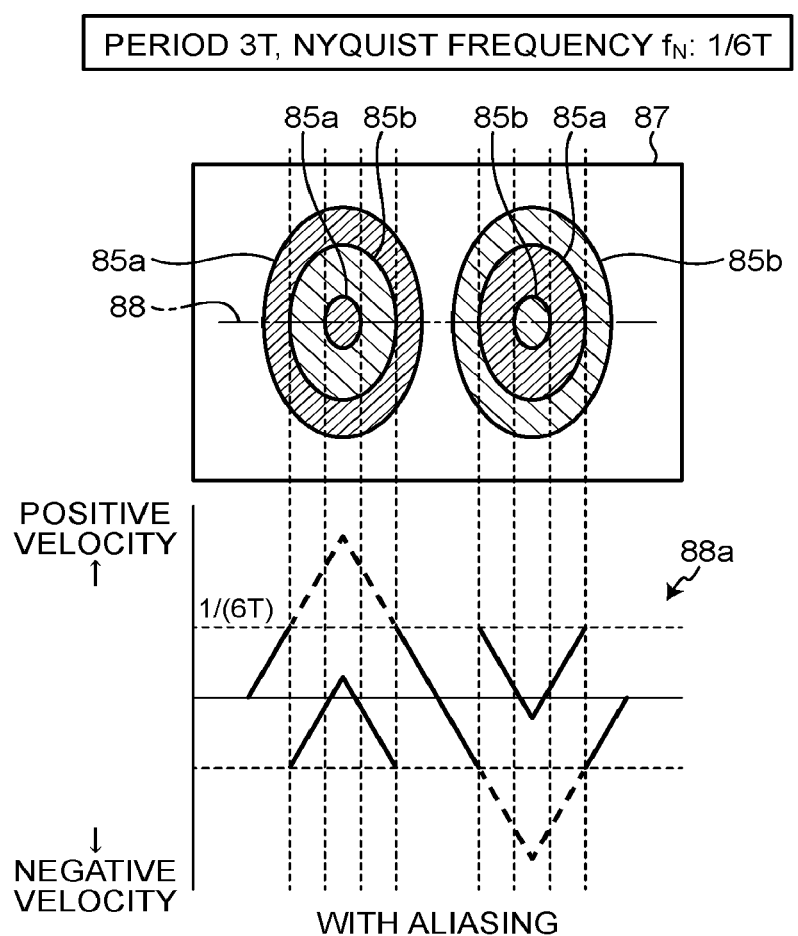

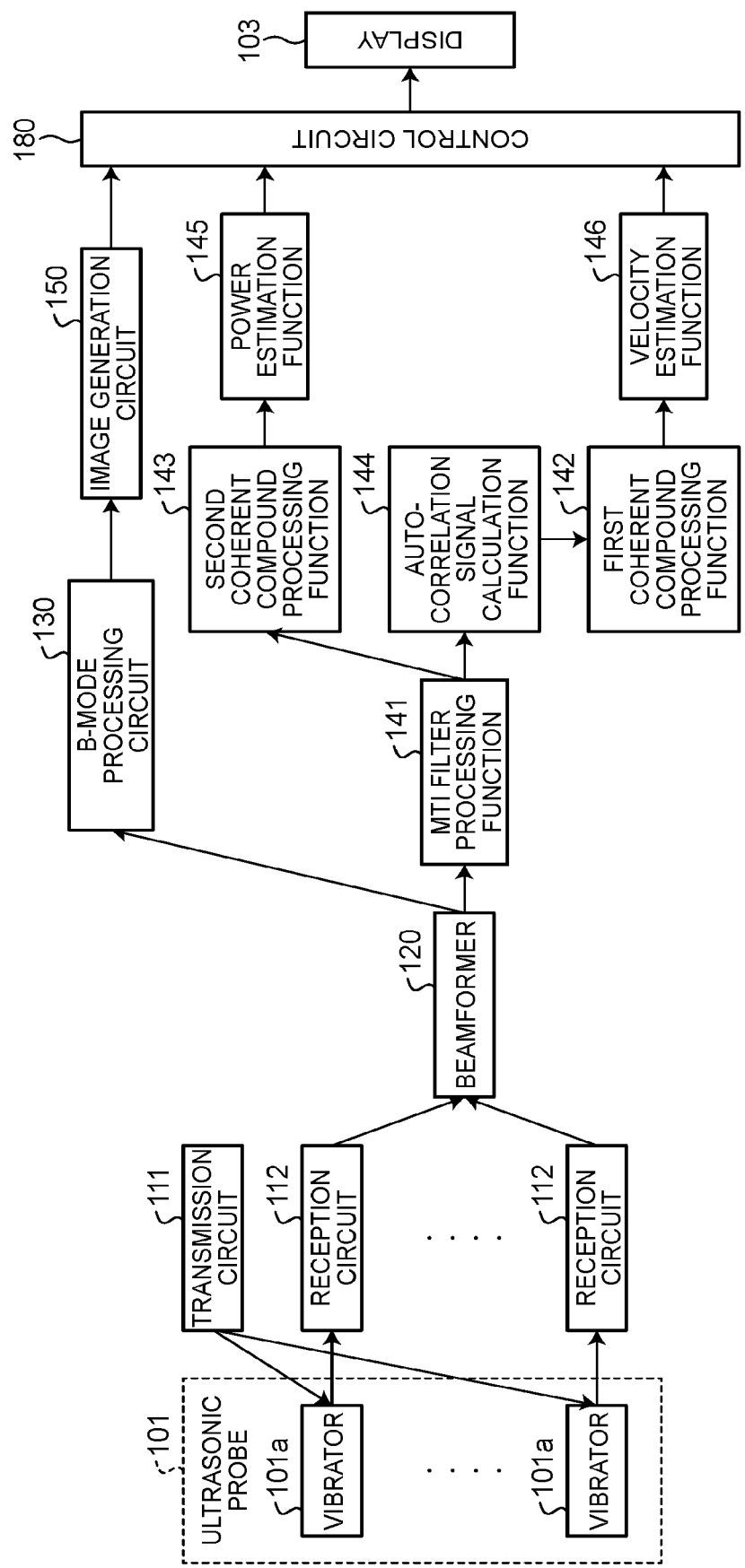

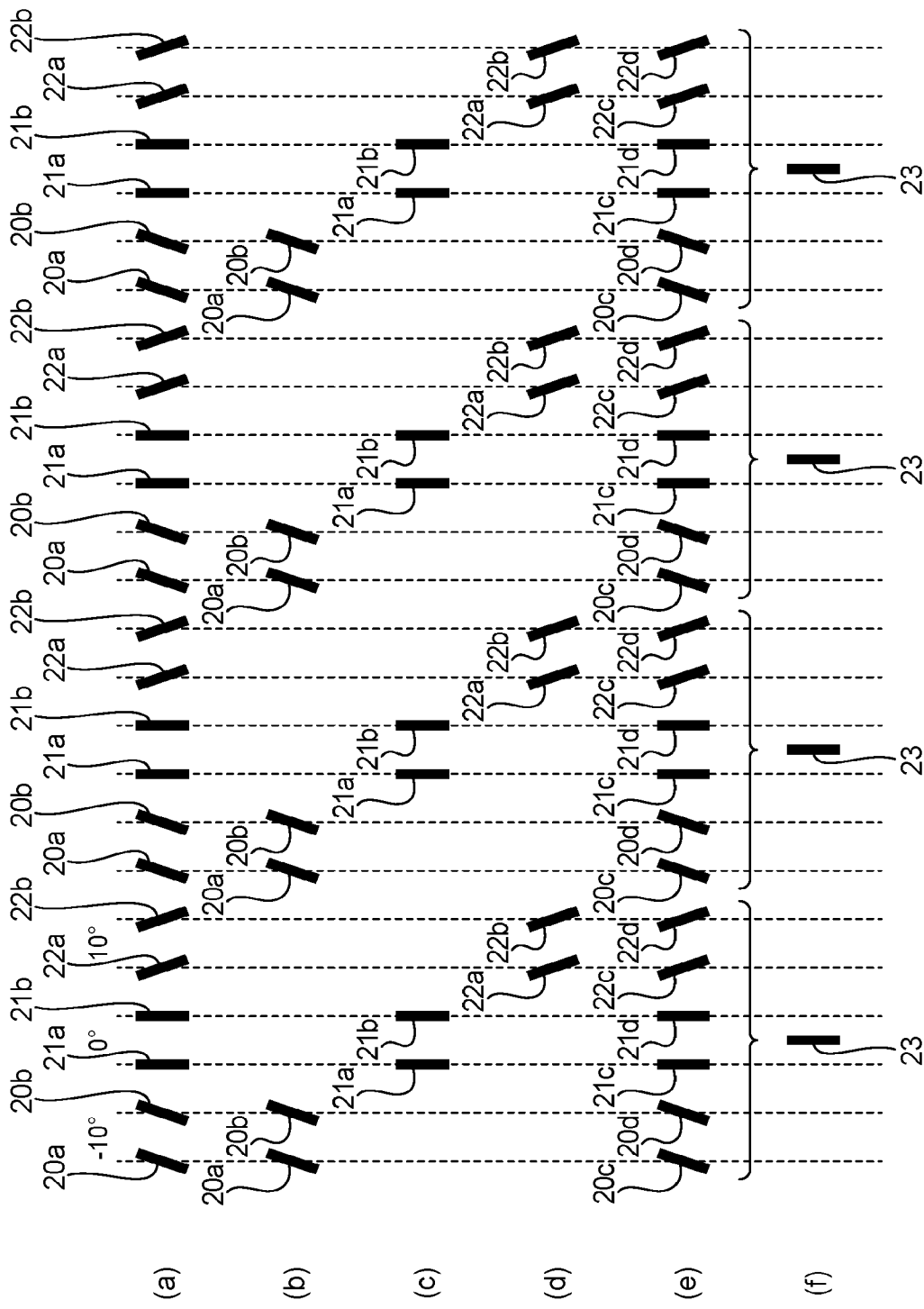

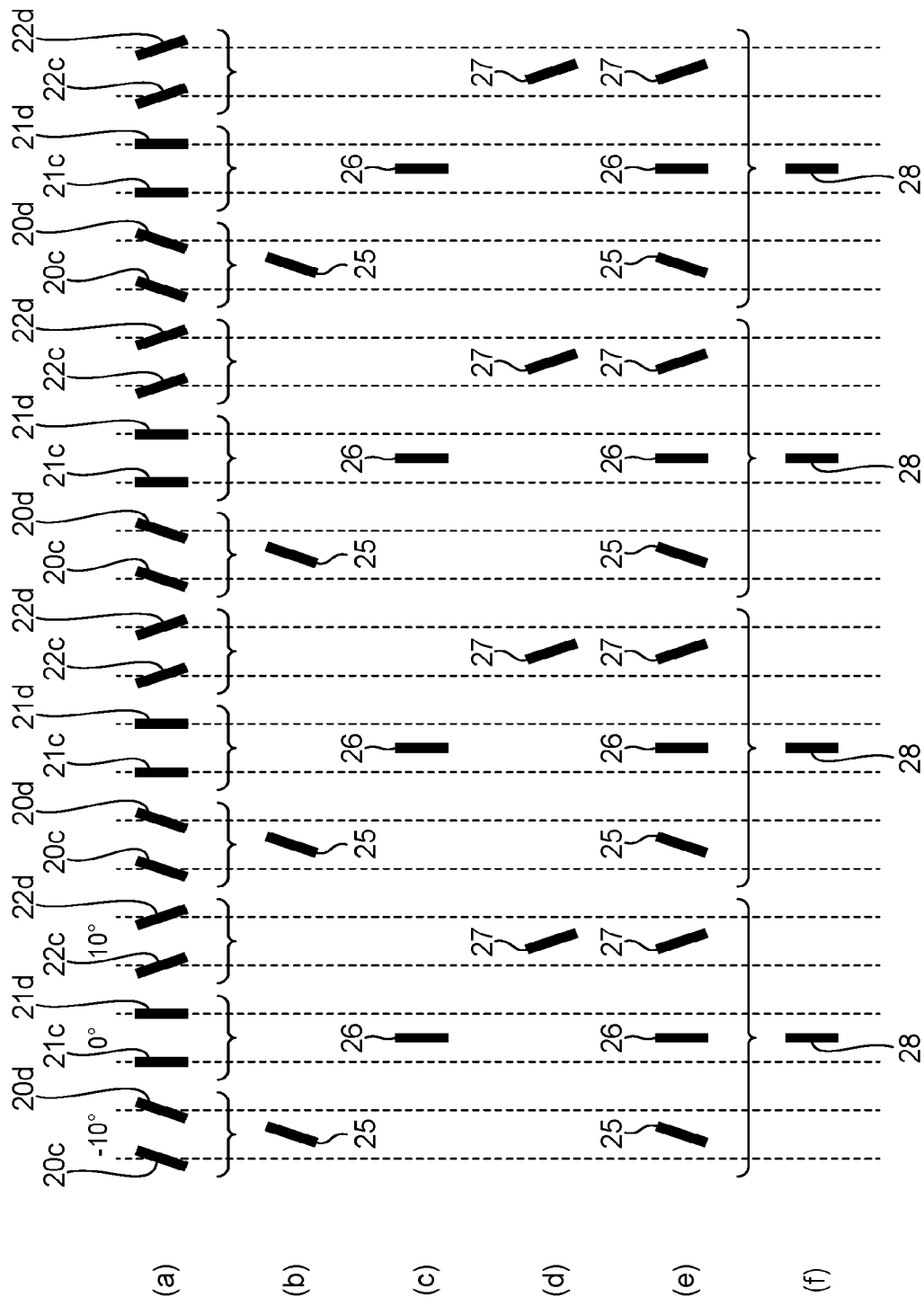

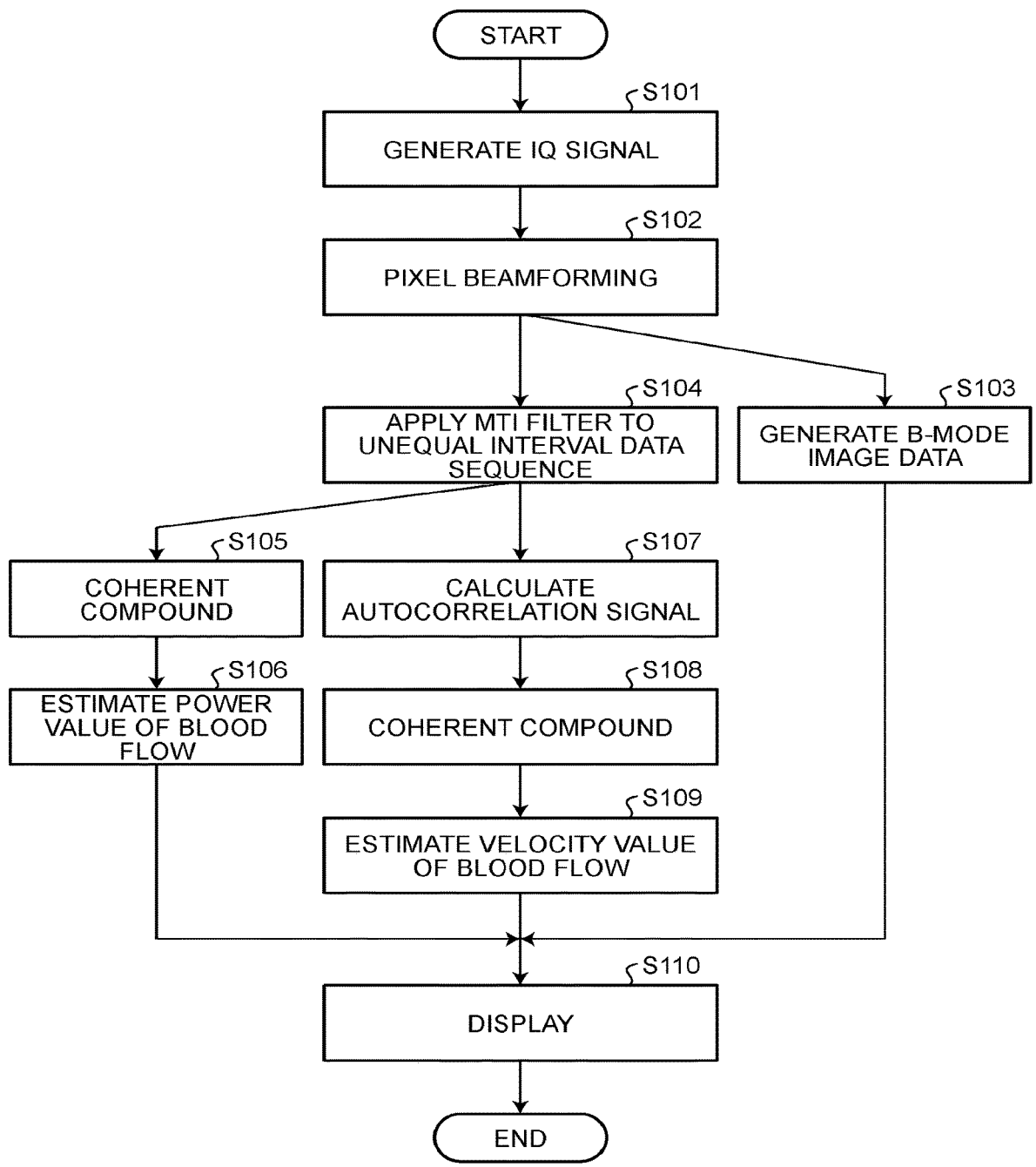

WITH ALIASING

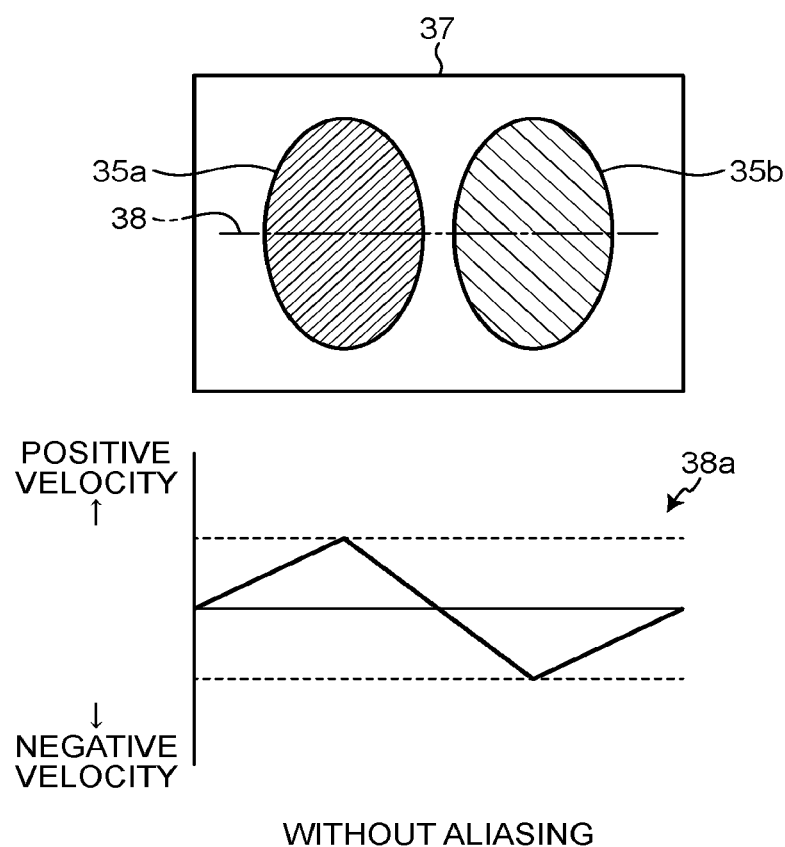

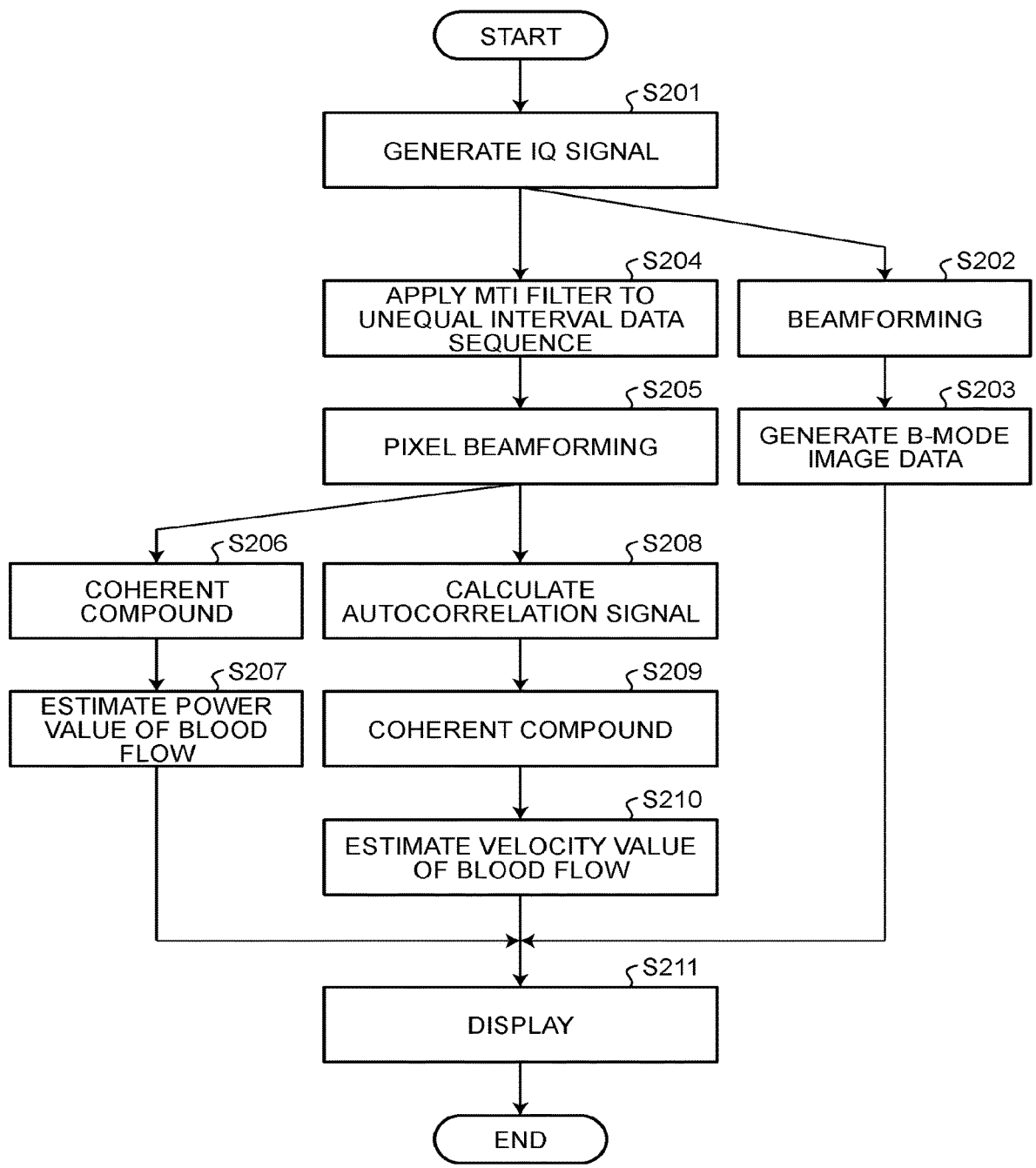

ULTRASONIC DIAGNOSTIC APPARATUS AND IMAGE PROCESSING APPARATUS

CROSS-REFERENCE TO RELATED APPLICATIONS

This application is based upon and claims the benefit of priority from Japanese Patent Application No. 2022-012638, filed on Jan. 31, 2022; the entire contents of which are incorporated herein by reference.

FIELD

Embodiments disclosed in the present specification and the drawings relate to an ultrasonic diagnostic apparatus and an image processing apparatus.

BACKGROUND

There is known a technique of beamforming each of a plurality of reception signals obtained by transmitting a plane wave in a plurality of directions, and coherently adding (compounding) signals at the same position after the beamforming. Such a technique is also called a plane wave coherent compound technique. Note that "coherently adding" is also referred to as "coherent compound". In addition, a method of applying a plane wave coherent technology to a color Doppler is known. Such a method is also referred to as an "Ultra Fast Doppler method".

In the "Ultra Fast Doppler method", a plurality of reception signals obtained by plane wave transmission in a plurality of directions with a repetition period T (1/PRF (Pulse Repetition Frequency)) is beamformed, and signals at the same position are coherently added. This is repeated a plurality of times. In the following description, the number of directions in which plane waves are transmitted is denoted by "A". In this case, the period of the coherent compounded signal sequence is AT (A/PRF). Therefore, in a case where the plane wave is transmitted in one direction, an aliasing frequency of Doppler is PRF/2, but in a case where the period of the compounded signal sequence is AT, the return frequency is PRF/2A. Thus, the aliasing frequency becomes 1/A times and decreases.

FIG. 1 is a diagram for describing an example of a conventional coherent compound. FIG. 1 illustrates a case where A=3. Here, a case where a plane wave is transmitted in three directions of the first direction, the second direction B, and the third direction will be described. In the example illustrated in FIG. 1, a signal (addition signal, complex signal) 84 is obtained by coherently adding a reception signal 81 obtained by transmitting a plane wave in the first direction, a reception signal 82 obtained by transmitting a plane wave in the second direction, and a reception signal 83 obtained by transmitting a plane wave in the third direction. Color Doppler processing is performed on the signal 84. That is, a moving target indicator (MTI) filter is applied to the signal 84. Then, this processing is repeated a plurality of times. Then, a result of the color Doppler processing is displayed. Note that the transmission interval of the plane wave is "T", and the transmission interval between two signals 84 adjacent on the time axis is "3T".

FIG. 2A is a diagram illustrating an example of display of a color Doppler in a case where a plane wave is transmitted in one direction, and FIG. 2B is a diagram illustrating an example of display of a color Doppler in a case where a plane wave is transmitted in three directions and coherent compound is performed as illustrated in FIG. 1.

In FIG. 2A, an image 85 illustrates a blood flow 85a approaching and a blood flow 85b moving away. FIG. 2A illustrates a velocity profile 86a on a line segment 86. Positive velocity is the velocity of the blood flow 85a approaching and negative velocity is the velocity of the blood flow 85b moving away.

In FIG. 2B, an image 87 illustrates the blood flow 85a approaching and the blood flow 85b moving away. FIG. 2B illustrates a velocity profile 88a on a line segment 88. Again, positive velocity is the velocity of the blood flow 85a approaching and negative velocity is the velocity of the blood flow 85b moving away.

In FIG. 2A, the blood flows 85a and 85b displayed without aliasing are displayed as double aliasing since the aliasing velocity is ⅓ times in FIG. 2B. Such aliasing has a problem that the direction of blood flow is misrecognized or the blood flow rate is underestimated.

In a case where the PRF is 10 kHz with an ultrasonic pulse having a center frequency of 5 MHz, the aliasing velocity of the color Doppler by packet method when normal focus transmission not using a plane wave coherent compound is $C \cdot PRF/4f_0 = 1540*10e3/(4*5e6) = 0.77$ m/s. In a case where the normal carotid artery is targeted, the almost no aliasing occurs at this aliasing velocity. On the other hand, in a case where a multidirectional plane wave coherent compound is used at A=5, the aliasing velocity becomes 0.154 m/s, which is ⅕ times, and there is a high possibility of aliasing.

Note that the frame rate in a case where the number of transmission rasters of normal color Doppler is "M" is M/PRF, whereas the frame rate in a case of the multidirectional plane wave coherent compound is A/PRF. Thus, for example, in a case where M=100 and A=5, the frame rate of the multidirectional plane wave coherent compound is usually 20 times that of the normal color Doppler. Thus, the multidirectional plane wave coherent compound is very useful when the user wants to observe blood flow at a high frame rate.

Accordingly, in a case where a multidirectional plane wave transmission compound is applied to the color Doppler, there is a demand to improve the aliasing velocity to PRF/2 similarly to the normal color Doppler.

An example of the simplest method for satisfying this demand will be described with reference to FIG. 3. FIG. 3 is a diagram for describing an example of a method of improving the aliasing velocity to PRF/2. A method for satisfying the above requirement is hereinafter referred to as "method 1". As method 1, for example, there is a method of continuously performing a plurality of times of packet transmission in the same direction. (a) of FIG. 3 illustrates scanning in a case where A=3 and the number of packets (the number of ensembles) E=2. For example, an ultrasonic transmission 90 is ultrasonic transmission with a deflection angle of −10°. An ultrasonic transmission 91 is ultrasonic transmission with a deflection angle of 0°. An ultrasonic transmission 92 is ultrasonic transmission with a deflection angle of 10°. In method 1, by repeating each of the ultrasonic transmission 90, the ultrasonic transmission 91, and the ultrasonic transmission 92 twice, ultrasonic waves are transmitted in three directions. Then, such scanning is repeatedly executed as illustrated in FIG. 3.

A reception signal (reception data) 90a illustrated in (b) of FIG. 3 is a reception signal obtained by the first-time (first) ultrasonic transmission 90 of two consecutive ultrasonic transmissions 90. Further, a reception signal 90b in (c) of FIG. 3 is a reception signal obtained by the second-time (second) ultrasonic transmission 90 out of the two consecutive ultrasonic transmissions 90.

A reception signal 91a illustrated in (d) of FIG. 3 is a reception signal obtained by the first ultrasonic transmission 91 of two consecutive ultrasonic transmissions 91. In addition, a reception signal 91b illustrated in (e) of FIG. 3 is a reception signal obtained by the second ultrasonic transmission 91 of the two consecutive ultrasonic transmissions 91.

A reception signal 92a illustrated in (f) of FIG. 3 is a reception signal obtained by the first ultrasonic transmission 92 of two consecutive ultrasonic transmissions 92. In addition, a reception signal 92b illustrated in (g) of FIG. 3 is a reception signal obtained by the second ultrasonic transmission 92 of the two consecutive ultrasonic transmissions 92.

In method 1, an MTI filter is applied to a data sequence (signal sequence) including a plurality of reception signals 90a. Thus, the MTI filter suppresses a signal (clutter signal) derived from a stationary tissue or a slow-moving tissue from the data sequence, and extracts a signal (blood flow signal) derived from blood flow. Then, the MTI filter outputs a blood flow signal.

For example, the MTI filter extracts a blood flow signal from a data sequence including the plurality of reception signals 90a, and outputs the extracted blood flow signal 90c. Similarly, in method 1, the MTI filter is applied to a data sequence including a plurality of reception signals 90b. Thus, the MTI filter outputs a blood flow signal 90d. Further, the MTI filter is applied to a data sequence including a plurality of reception signals 91a. Thus, the MTI filter outputs a blood flow signal 91c. Further, the MTI filter is applied to a data sequence including a plurality of reception signals 91b. Thus, the MTI filter outputs a blood flow signal 91d. Further, the MTI filter is applied to a data sequence including a plurality of reception signals 92a. Thus, the MTI filter outputs a blood flow signal 92c. Further, the MTI filter is applied to a data sequence including a plurality of reception signals 92b. Thus, the MTI filter outputs a blood flow signal 92d.

Then, as illustrated in (h) of FIG. 3, the outputs of the MTI filter are returned to the original order. FIG. 4 is a diagram illustrating an example of frequency characteristics of a data sequence including a plurality of blood flow signals arranged in (h) of FIG. 3. As illustrated in FIG. 4, a characteristic of each MTI filter is that the aliasing frequency is 1/(12T). However, by arranging a plurality of blood flow signals as illustrated in (h) of FIG. 3, the aliasing frequency is expanded to 1/(2T), and the characteristics of the MTI filter are as illustrated in FIG. 4. As can be seen from FIG. 4, a frequency at which the amplitude characteristic becomes zero, that is, a blind frequency occurs. This is not preferable because velocity estimation accuracy near the blind frequency is significantly reduced.

BRIEF DESCRIPTION OF THE DRAWINGS

FIG. 2A is a diagram illustrating an example of display of a color Doppler in a case where a plane wave is transmitted in one direction;

FIG. 2B is a diagram illustrating an example of display of a color Doppler in a case where a plane wave is transmitted in three directions and coherent compound is performed as illustrated in FIG. 1;

FIG. 5B is a diagram for describing an example of a flow of various types of information (data, signals, and the like) between respective units (each circuit, each function, and the like) included in the ultrasonic diagnostic apparatus according to the first embodiment;

FIG. 6 is a diagram for describing an example of processing in which the ultrasonic diagnostic apparatus according to the first embodiment estimates a power value of blood flow;

FIG. 7 is a diagram for describing an example of processing in which the ultrasonic diagnostic apparatus according to the first embodiment estimates a velocity value of blood flow;

FIG. 9 is a flowchart illustrating a flow of an example of processing executed by the ultrasonic diagnostic apparatus according to the first embodiment;

FIG. 10B is a diagram illustrating an example of display of a color Doppler obtained by the ultrasonic diagnostic apparatus according to the first embodiment;

FIG. 12 is a flowchart illustrating a flow of an example of processing executed by the ultrasonic diagnostic apparatus according to the second embodiment.

DETAILED DESCRIPTION

Figure 1:
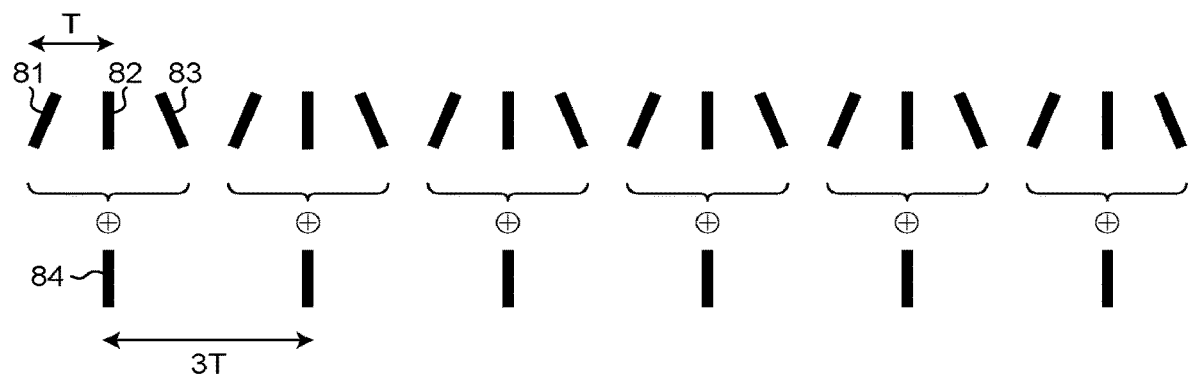
FIG. 1 is a diagram for describing an example of a conventional coherent compound.

An ultrasonic diagnostic apparatus of an embodiment includes an ultrasonic probe and processing circuitry. The ultrasonic probe repeatedly performs scanning in which a plane wave or a diffused wave is continuously transmitted a plurality of times in the same direction in a plurality of directions. The processing circuitry performs processing of applying a moving target indicator (MTI) filter to an unequal interval data sequence in the same direction obtained by the scanning and extracting a blood flow signal in each of the plurality of directions, performs processing of generating an autocorrelation signal by performing an autocorrelation operation on a plurality of blood flow signals in the same direction for each of the directions, and estimates a velocity value of blood flow on the basis of a complex signal generated by performing complex addition of a plurality of autocorrelation signals generated for the plurality of directions.

Hereinafter, an ultrasonic diagnostic apparatus and an image processing apparatus according to embodiments will be described with reference to the drawings. Note that the embodiment can be combined with the prior art, another embodiment, or another modification as long as there is no contradiction in the contents. Similarly, the modification can be combined with the prior art, another embodiment, or another modification as long as there is no contradiction in the contents. In the following description, the same components are denoted by the same reference numerals, and redundant description may be omitted.

First Embodiment

Figure 5A:
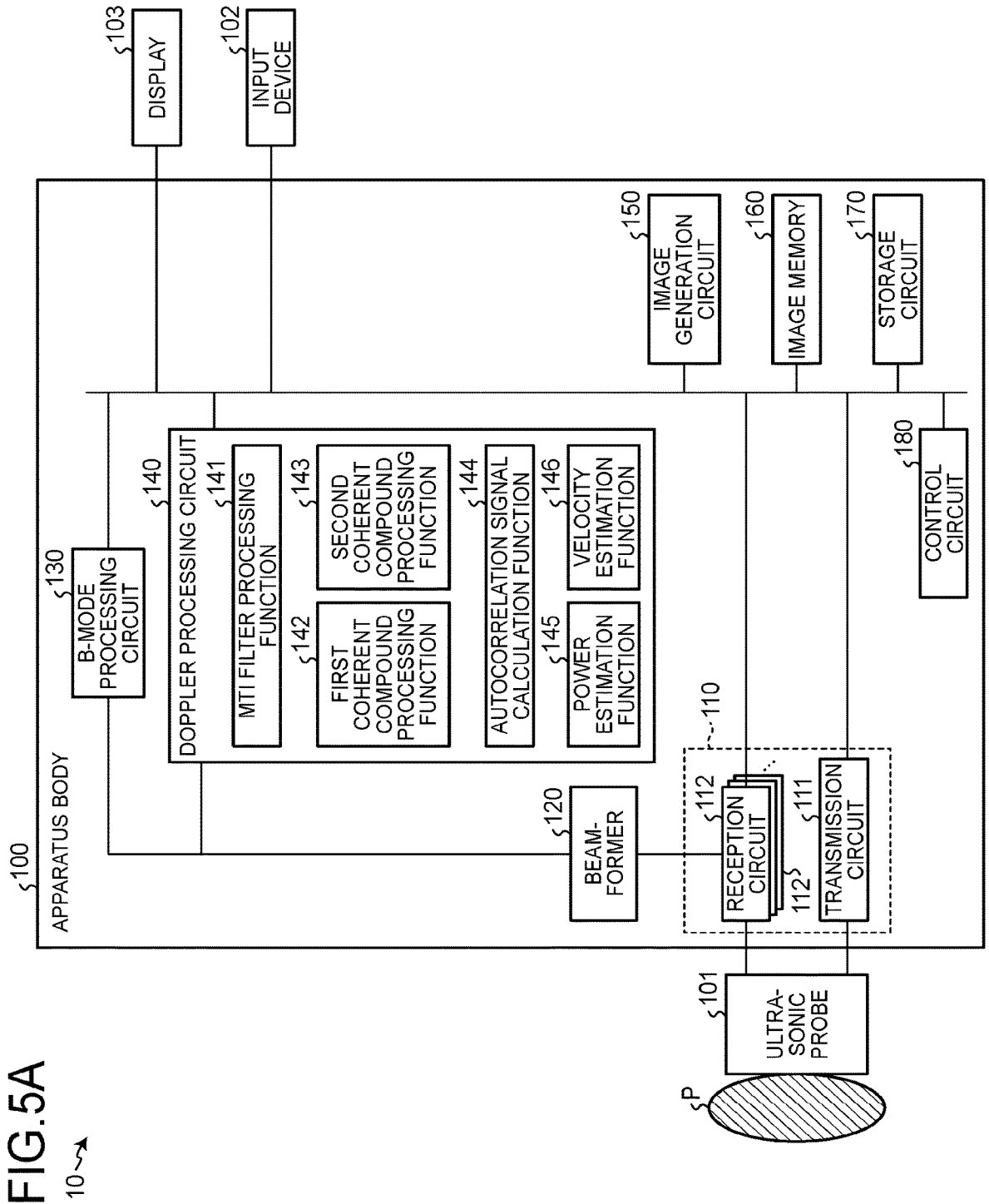
FIG. 5A is a block diagram illustrating a configuration example of an ultrasonic diagnostic apparatus according to a first embodiment.

FIG. 5A is a block diagram illustrating a configuration example of an ultrasonic diagnostic apparatus 10 according to the first embodiment. As illustrated in FIG. 5A, an ultrasonic diagnostic apparatus 10 according to the first embodiment includes an apparatus body 100, an ultrasonic probe 101, an input device 102, and a display 103.

The ultrasonic probe 101 includes, for example, a plurality of vibrators (piezoelectric elements) 101a (see FIG. 5B described later). The plurality of vibrators 101a generates an ultrasonic wave on the basis of a drive signal supplied from a transmission circuit 111 of a transmission/reception circuit 110 included in the apparatus body 100. Specifically, when a voltage (transmission driving voltage) is applied by the transmission circuit 111, the plurality of vibrators 101a generates an ultrasonic wave having a waveform corresponding to the transmission driving voltage. Further, the ultrasonic probe 101 receives a reflected wave from the subject P, converts the reflected wave into a reflected wave signal that is an electric signal, and outputs (transmits) the reflected wave signal to the apparatus body 100. Furthermore, the ultrasonic probe 101 includes, for example, a matching layer provided on the vibrator 101a, a backing material that prevents propagation of an ultrasonic wave rearward from the vibrator 101a, and the like. The ultrasonic probe 101 is detachably connected to the apparatus body 100.

When ultrasonic waves (transmission ultrasonic wave, ultrasonic pulse) are transmitted from the ultrasonic probe 101 to the subject P, the transmitted ultrasonic waves are reflected one after another on the discontinuous surface of the acoustic impedance in the body tissue of the subject P, and are received as reflected waves by the plurality of vibrators 101a included in the ultrasonic probe 101. The amplitude of the received reflected wave depends on the difference in acoustic impedance at the discontinuous surface from which the ultrasonic wave is reflected. Note that the reflected wave in a case where the transmitted ultrasonic pulse is reflected by the moving blood flow or the surface of the heart wall or the like is subjected to frequency shift depending on the velocity component with respect to the ultrasonic transmission direction of a moving body due to the Doppler effect. Then, the ultrasonic probe 101 transmits the reflected wave signal to a reception circuit 112 of the transmission/reception circuit 110 described later.

The ultrasonic probe 101 is detachably attached to the apparatus body 100. When scanning a two-dimensional region in the subject P (two-dimensional scanning), the operator connects, for example, a 1D array probe in which a plurality of vibrators 101a is arranged in a line to the apparatus body 100 as the ultrasonic probe 101. Examples of the type of the 1D array probe include a linear type ultrasonic probe, a convex type ultrasonic probe, and a sector type ultrasonic probe. Further, when scanning a three-dimensional region in the subject P (three-dimensional scanning) is performed, the operator connects, for example, a mechanical 4D probe or a 2D array probe as the ultrasonic probe 101 to the apparatus body 100. The mechanical 4D probe can perform two-dimensional scanning using a plurality of vibrators 101a arranged in a line like a 1D array probe, and can perform three-dimensional scanning by swinging the plurality of vibrators 101a at a predetermined angle (swing angle). In addition, the 2D array probe can perform three-dimensional scanning by a plurality of vibrators 101a arranged in a matrix, and can perform two-dimensional scanning by focusing and transmitting ultrasonic waves.

The input device 102 is implemented by, for example, an input means such as a mouse, a keyboard, a button, a panel switch, a touch command screen, a foot switch, a trackball, or a joystick. The input device 102 receives various setting requests from an operator of the ultrasonic diagnostic apparatus 10, and transfers the received various setting requests to the apparatus body 100.

The display 103 displays, for example, a graphical user interface (GUI) for the operator of the ultrasonic diagnostic apparatus 10 to input various setting requests using the input device 102, or displays an ultrasound image or the like based on the ultrasound image data generated in the apparatus body 100. The display 103 is implemented by a liquid crystal monitor, a cathode ray tube (CRT) monitor, or the like.

The apparatus body 100 generates ultrasound image data on the basis of the reflected wave signal transmitted from the ultrasonic probe 101. Note that the ultrasound image data is an example of the image data. The apparatus body 100 can generate two-dimensional ultrasound image data on the basis of the reflected wave signal corresponding to the two-dimensional region of the subject P transmitted from the ultrasonic probe 101. In addition, the apparatus body 100 can generate three-dimensional ultrasound image data on the basis of the reflected wave signal corresponding to the three-dimensional region of the subject P transmitted from the ultrasonic probe 101. As illustrated in FIGS. 5A and 5B, the apparatus body 100 includes the transmission/reception circuit 110, a beamformer 120, a B-mode processing circuit 130, a Doppler processing circuit 140, an image generation circuit 150, an image memory 160, a storage circuit 170, and a control circuit 180.

Under controlling of the control circuit 180, the transmission/reception circuit 110 causes the ultrasonic probe 101 to transmit an ultrasonic wave and causes the ultrasonic probe 101 to receive a reflected wave of the ultrasonic wave. That is, the transmission/reception circuit 110 executes scanning via the ultrasonic probe 101. Note that scanning is also referred to as scanning, ultrasonic scanning. The transmission/reception circuit 110 is an example of a transmission/reception unit. The transmission/reception circuit 110 includes a transmission circuit 111 and a plurality of reception circuits 112.

Under controlling of the control circuit 180, the transmission circuit 111 supplies a drive signal to the ultrasonic probe 101 and causes the ultrasonic probe 101 to transmit an ultrasonic wave. The transmission circuit 111 includes a rate pulser generation circuit, a transmission delay circuit, and a transmission pulser. When scanning a two-dimensional region in the subject P, the transmission circuit 111 causes the ultrasonic probe 101 to transmit an ultrasonic beam for scanning the two-dimensional region. Further, when scanning a three-dimensional region in the subject P, the transmission circuit 111 causes the ultrasonic probe 101 to transmit an ultrasonic beam for scanning the three-dimensional region.

Under controlling of the control circuit 180, the rate pulser generation circuit repeatedly generates a rate pulse for forming a transmission ultrasonic wave (transmission beam) at a predetermined rate frequency (pulse repetition frequency (PRF)). When the rate pulse passes through the transmission delay circuit, a voltage is applied to the transmission pulser in a state of having different transmission delay times. For example, the transmission delay circuit gives a transmission delay time for each vibrator 101a necessary for focusing the ultrasonic wave generated from the ultrasonic probe 101 in a beam shape and determining the transmission directivity to each rate pulse generated by the rate pulser generation circuit. The transmission pulser supplies a drive signal (drive pulse) to the ultrasonic probe 101 at timing based on the rate pulse. Note that the transmission delay circuit arbitrarily adjusts the transmission direction of the ultrasonic wave from the vibrator surface by changing the transmission delay time given to each rate pulse.

After the drive pulse is transmitted from the transmission pulser to the vibrator 101a in the ultrasonic probe 101 via the cable, the electrical signal is converted into mechanical vibration in the vibrator 101a. That is, when a voltage is applied to the vibrator 101a, the vibrator 101a mechanically vibrates. The ultrasonic wave generated by the mechanical vibration is transmitted to the inside of the living body. Here, ultrasonic waves having different transmission delay times for the respective vibrators 101a are focused and propagated in a predetermined direction.

Note that the transmission circuit 111 has a function capable of instantaneously changing a transmission frequency, a transmission driving voltage, and the like in order to execute a predetermined scanning sequence under controlling of the control circuit 180. In particular, the transmission driving voltage is changed by a linear amplifier type transmission circuit capable of instantaneously switching the value of the transmission driving voltage or a mechanism for electrically switching a plurality of power supply units.

After the reflected wave of the ultrasonic wave transmitted by the ultrasonic probe 101 reaches the vibrator 101a inside the ultrasonic probe 101, the mechanical vibration is converted into an electrical signal (reflected wave signal) in the vibrator 101a, and the converted reflected wave signal is input to the reception circuit 112. That is, an analog reflected wave signal is input to the reception circuit 112. The reception circuit 112 includes a low noise amplifier (LNA), an analog time gain compensation (ATGC) processing circuit, an analog to digital converter (ADC), a demodulator, and the like, performs various processes on the reflected wave signal transmitted from the ultrasonic probe 101, and generates an in-phase signal (I signal, I: In-phase) and a quadrature signal (Q signal, Q: Quadrature-phase) in a baseband band as a reflected wave signal in a digital format. The I signal and the Q signal are called IQ signals. Then, the reception circuit 112 transmits the generated IQ signal to the beamformer 120 as a reflected wave signal (reception signal).

In the present embodiment, one reception circuit 112 is provided corresponding to one channel. Here, one channel corresponds to one vibrator 101a. Thus, one reception circuit 112 is provided corresponding to one vibrator 101a. Therefore, the transmission/reception circuit 110 includes each of the plurality of reception circuits 112 corresponding to each of the plurality of vibrators 101a.

The beamformer 120 generates reflected wave data by performing beamforming (phasing addition) on the reflected wave signals transmitted by the plurality of reception circuits 112. Note that the reflected wave signal (IQ signal) and the reflected wave data are examples of reception signals. The beamformer 120 transmits the generated reflected wave data to the B-mode processing circuit 130 and the Doppler processing circuit 140. The beamformer 120 is implemented by, for example, a processor. The beamformer 120 is an example of a beamforming processor. Details of the beamformer 120 will be described later.

The B-mode processing circuit 130 receives the reflected wave data transmitted by the beamformer 120, performs various types of signal processing on the received reflected wave data, and transmits the reflected wave data subjected to the various types of signal processing to the image generation circuit 150 as B-mode data. The B-mode processing circuit 130 is implemented by, for example, a processor. The B-mode processing circuit 130 is an example of a B-mode processor. Hereinafter, an example of the various types of signal processing executed by the B-mode processing circuit 130 will be described.

For example, the B-mode processing circuit 130 performs various types of processing such as envelope detection processing and logarithmic compression on the reflected wave data to generate the B-mode data in which signal intensity (amplitude intensity) of each sample point is expressed by brightness of luminance. For example, the B-mode processing circuit 130 includes an envelope detector, a logarithmic compression device, and the like. For example, the envelope detector performs envelope detection on the reflected wave data, and a logarithmic compressor logarithmically compresses data (for example, data indicating amplitude or the like) related to the envelope obtained by the envelope detection. Thus, the B-mode data is generated. The B-mode processing circuit 130 transmits the generated B-mode data to the image generation circuit 150.

In addition, the B-mode processing circuit 130 executes signal processing for performing harmonic imaging for visualizing harmonic components. Examples of the harmonic imaging include CHI and THI. In addition, in CHI and THI, for example, phase modulation (PM) called pulse inversion method is known as a scanning method.

The Doppler processing circuit 140 receives the reflected wave data transmitted by the beamformer 120, performs various types of signal processing on the received reflected wave data, and transmits the reflected wave data subjected to the various types of signal processing to the image generation circuit 150 as Doppler data. The Doppler processing circuit 140 is implemented by, for example, a processor. The Doppler processing circuit 140 is an example of a Doppler processor. Hereinafter, an example of the various types of signal processing executed by the Doppler processing circuit 140 will be described.

The Doppler processing circuit 140 extracts motion information of a moving body (blood flow, tissue, contrast agent echo component, and the like) based on the Doppler effect from the reflected wave data by performing frequency analysis on the reflected wave data, and generates the Doppler data indicating the extracted motion information. For example, the Doppler processing circuit 140 extracts average velocity, an average variance value and an average power value, and the like over multiple points as the motion information of the moving body, and generates the Doppler data indicating the extracted motion information of the moving body. The Doppler processing circuit 140 transmits the generated Doppler data to the image generation circuit 150.

Using the above-described function of the Doppler processing circuit 140, the ultrasonic diagnostic apparatus 10 can execute a color Doppler method also called a color flow mapping (CFM) method. In the color flow mapping method, ultrasonic waves are transmitted and received a plurality of times on a plurality of scanning lines. Then, in the color flow mapping method, a moving target indicator (MTI) filter is applied to the data sequence at the same position to suppress a signal (clutter signal) derived from a stationary tissue or a slow-moving tissue from the data sequence at the same position and extract a signal (blood flow signal) derived from blood flow. Then, in the color flow mapping method, blood flow information such as a velocity (velocity value) of blood flow, a variance (variance value) of blood flow, and power (power value) of blood flow is estimated from the blood flow signal. The Doppler processing circuit 140 transmits color image data indicating the blood flow information estimated by the color flow mapping method to the image generation circuit 150. Note that the color image data is an example of the Doppler data.

The B-mode processing circuit 130 and the Doppler processing circuit 140 can process reflected wave data of both two-dimensional reflected wave data and three-dimensional reflected wave data.

The image generation circuit 150 generates ultrasound image data from the B-mode data transmitted by the B-mode processing circuit 130 and the Doppler data transmitted by the Doppler processing circuit 140. The image generation circuit 150 is implemented by a processor.

For example, the image generation circuit 150 generates two-dimensional B-mode image data in which the intensity of a reflected wave is represented by luminance from the two-dimensional B-mode data generated by the B-mode processing circuit 130. In addition, the image generation circuit 150 generates two-dimensional Doppler image data in which the motion information or the blood flow information is visualized from the two-dimensional Doppler data generated by the Doppler processing circuit 140. Note that the two-dimensional Doppler image data obtained by visualizing the motion information is velocity image data, variance image data, power image data, or image data obtained by combining these.

Here, the image generation circuit 150 generally converts (scan converts) a scanning line signal sequence of ultrasonic scanning into a scanning line signal sequence of a video format represented by television or the like, and generates ultrasound image data for display. For example, the image generation circuit 150 performs coordinate conversion on the data transmitted by the B-mode processing circuit 130 or the Doppler processing circuit 140 according to the scanning mode of the ultrasonic wave by the ultrasonic probe 101, thereby generating ultrasound image data for display. Further, the image generation circuit 150 performs, for example, image processing (smoothing processing) of regenerating an average value image of luminance using a plurality of image frames after the scan conversion, image processing (edge enhancement processing) using a differential filter in an image, and the like as various types of image processing other than the scan conversion. In addition, the image generation circuit 150 synthesizes character information, graduations, body marks, and the like of various parameters with the ultrasound image data.

Furthermore, the image generation circuit 150 generates three-dimensional B-mode image data by performing coordinate conversion on the three-dimensional B-mode data generated by the B-mode processing circuit 130. In addition, the image generation circuit 150 generates three-dimensional Doppler image data by performing coordinate conversion on the three-dimensional Doppler data generated by the Doppler processing circuit 140. That is, the image generation circuit 150 generates "three-dimensional B-mode image data and three-dimensional Doppler image data" as "three-dimensional ultrasound image data (volume data)". Then, the image generation circuit 150 performs various types of rendering processing on the volume data in order to generate various types of two-dimensional image data for displaying the volume data on the display 103.

The rendering processing performed by the image generation circuit 150 includes, for example, processing of generating MPR image data from volume data using a cross section reconstruction method (MPR: multi-planar reconstruction). Furthermore, examples of the rendering processing performed by the image generation circuit 150 include volume rendering (VR) processing for generating two-dimensional image data reflecting three-dimensional information. The image generation circuit 150 is an example of an image generator.

The B-mode data and the Doppler data are ultrasound image data before the scan conversion processing, and the data generated by the image generation circuit 150 is ultrasound image data for display after the scan conversion processing. Note that the B-mode data and the Doppler data are also referred to as raw data.

The image memory 160 is a memory that stores various image data generated by the image generation circuit 150. Further, the image memory 160 also stores data generated by the B-mode processing circuit 130 or the Doppler processing circuit 140. The B-mode data and Doppler data stored in the image memory 160 can be called by an operator after diagnosis, for example, and become ultrasound image data for display via the image generation circuit 150. For example, the image memory 160 is implemented by a random access memory (RAM), a semiconductor memory element such as a flash memory, a hard disk, or an optical disk.

The storage circuit 170 stores control programs for performing scanning (transmission and reception of ultrasonic waves), image processing, and display processing, diagnostic information (for example, patient ID, doctor's finding, and the like), and various data such as diagnostic protocols and various body marks. In addition, the storage circuit 170 is also used to store data stored in the image memory 160 as necessary. For example, the storage circuit 170 is implemented by a semiconductor memory element such as a flash memory, a hard disk, or an optical disk.

The control circuit 180 controls the entire processing of the ultrasonic diagnostic apparatus 10. Specifically, the control circuit 180 controls processing of the transmission/reception circuit 110, the beamformer 120, the B-mode processing circuit 130, the Doppler processing circuit 140, and the image generation circuit 150 on the basis of various setting requests input from the operator via the input device 102 and various control programs and various data read from the storage circuit 170. In addition, the control circuit 180 controls the display 103 to display an ultrasound image based on the ultrasound image data for display stored in the image memory 160. For example, the control circuit 180 controls the display 103 to display a B-mode image based on the B-mode image data or a color image based on the color image data. Furthermore, the control circuit 180 controls the display 103 to display a color image superimposed on the B-mode image. The control circuit 180 is an example of a display control unit or a control unit. The control circuit 180 is implemented by, for example, a processor. The ultrasound image is an example of an image.

Furthermore, the control circuit 180 controls the ultrasonic probe 101 via the transmission/reception circuit 110 to control the ultrasonic scanning.

The overall configuration of the ultrasonic diagnostic apparatus 10 according to the first embodiment has been described above. The ultrasonic diagnostic apparatus 10 executes various processes described below in order to suppress a decrease in the aliasing velocity in a case where the multidirectional plane wave transmission compound is applied to the color Doppler.

As illustrated in FIG. 5A, the Doppler processing circuit 140 has an MTI filter processing function 141, a first coherent compound processing function 142, a second coherent compound processing function 143, an autocorrelation signal calculation function 144, a power estimation function 145, and a velocity estimation function 146. Here, the MTI filter processing function 141 is an example of an MTI filter processor. In addition, the first coherent compound processing function 142 and the second coherent compound processing function 143 are examples of an addition unit. Further, the autocorrelation signal calculation function 144, the power estimation function 145, and the velocity estimation function 146 are examples of an estimation unit.

Here, for example, the respective processing functions of the MTI filter processing function 141, the first coherent compound processing function 142, the second coherent compound processing function 143, the autocorrelation signal calculation function 144, the power estimation function 145, and the velocity estimation function 146, which are components of the Doppler processing circuit 140 illustrated in FIG. 5A, are recorded in a storage device (for example, the storage circuit 170) of the ultrasonic diagnostic apparatus 10 in the form of a program executable by a computer. The Doppler processing circuit 140 is a processor that implements each function corresponding to each program by reading each program from the storage device and executing each read program. In other words, the Doppler processing circuit 140 in a state of reading each program has each function illustrated in the Doppler processing circuit 140 of FIG. 5A. Processes executed by the respective processing functions of the MTI filter processing function 141, the first coherent compound processing function 142, the second coherent compound processing function 143, the autocorrelation signal calculation function 144, the power estimation function 145, and the velocity estimation function 146 will be described later.

Next, an example of processing executed by the ultrasonic diagnostic apparatus 10 will be described. FIGS. 5B, 6, and 7 are diagrams for describing an example of processing executed by the ultrasonic diagnostic apparatus 10 according to the first embodiment. More specifically, FIG. 5B is a diagram for describing an example of a flow of various types of information (data, signals, and the like) between respective units (each circuit, each function, and the like) included in the ultrasonic diagnostic apparatus 10. In addition, FIG. 6 is a diagram for describing an example of processing in which the ultrasonic diagnostic apparatus 10 estimates the power value of blood flow. Further, FIG. 7 is a diagram for describing an example of processing in which the ultrasonic diagnostic apparatus 10 estimates a velocity value of blood flow.

In the first embodiment, a processing system that generates the B-mode image, a processing system that estimates the power value of blood flow, and a processing system that estimates the velocity value of blood flow are divided at a stage subsequent to the beamformer 120. Thus, for example, the power value of blood flow and the velocity value of blood flow are estimated independently. The processing system that generates the B-mode image includes a B-mode processing circuit 130 and an image generation circuit 150. The processing system for estimating the power value of blood flow includes the MTI filter processing function 141, the second coherent compound processing function 143, and the power estimation function 145. The processing system for estimating the velocity value of blood flow includes the MTI filter processing function 141, the autocorrelation signal calculation function 144, the first coherent compound processing function 142, and the velocity estimation function 146.

First, an example of processing in which the ultrasonic diagnostic apparatus 10 estimates the power value of blood flow will be described with reference to FIGS. 5B and 6. The ultrasonic probe 101 operates as follows under controlling of the transmission circuit 111. For example, the ultrasonic probe 101 transmits a plane wave in a direction A (A is a natural number and is plural). In addition, the ultrasonic probe 101 continuously transmits plane waves E (which is a natural number and is plural) in each direction. In the following description, a case where A=3 and E=2 will be described. That is, a case where the ultrasonic probe 101 transmits plane waves in three directions and continuously transmits plane waves twice in each direction will be described as an example. For example, the ultrasonic probe 101 transmits a plane wave in three directions of a direction of a deflection angle of −10°, a direction of a deflection angle of 0°, and a direction of a deflection angle of 10°.

The ultrasonic probe 101 transmits a plane wave in a pulse repetition period T (1/PRF). That is, the transmission interval of the plane wave is the pulse repetition period T.

Then, the ultrasonic probe 101 transmits plane waves in three directions, and repeats scanning in which plane waves are continuously transmitted twice in each direction. That is, the ultrasonic probe 101 repeatedly performs scanning in which plane waves are continuously transmitted a plurality of times in the same direction in a plurality of directions.

As illustrated in FIG. 5B, each of the plurality of reception circuits 112 is connected to each of the plurality of vibrators 101a. Further, each of the plurality of reception circuits 112 is connected to the beamformer 120. Then, the reflected wave signal transmitted from each of the plurality of vibrators 101a is input to each of the plurality of reception circuits 112.

In the present embodiment, the reception circuit 112 generates an IQ signal (reception signal) on the basis of the reflected wave signal transmitted from the ultrasonic probe 101 and derived from the plane wave transmitted in the direction of the deflection angle of −10°, and transmits the generated IQ signal to the beamformer 120. Hereinafter, such an IQ signal based on the reflected wave signal derived from the plane wave transmitted in the direction of the deflection angle of −10° is referred to as a "first IQ signal". Note that, since the plane wave is continuously transmitted twice in the direction of the deflection angle of −10°, the IQ signal based on the reflected wave signal derived from the plane wave transmitted for the first time (first) is denoted as "first IQ signal (1)", and the IQ signal based on the reflected wave signal derived from the plane wave transmitted for the second time (second) is denoted as "first IQ signal (2)".

Similarly, the reception circuit 112 generates an IQ signal on the basis of the reflected wave signal transmitted from the ultrasonic probe 101 and derived from the plane wave transmitted in the direction of the deflection angle of 0°, and transmits the generated IQ signal to the beamformer 120. Hereinafter, such an IQ signal based on the reflected wave signal derived from the plane wave transmitted in the direction of the deflection angle of 0° is referred to as a "second IQ signal". Note that, since the plane wave is continuously transmitted twice in the direction of the deflection angle of 0°, the IQ signal based on the reflected wave signal derived from the plane wave transmitted for the first time is denoted as "second IQ signal (1)", and the IQ signal based on the reflected wave signal derived from the plane wave transmitted for the second time is denoted as "second IQ signal (2)".

In addition, the reception circuit 112 generates an IQ signal on the basis of the reflected wave signal transmitted from the ultrasonic probe 101 and derived from the plane wave transmitted in the direction of the deflection angle of 10°, and transmits the generated IQ signal to the beamformer 120. For example, the reception circuit 112 generates a plurality of IQ signals by transmitting a plane wave once. Hereinafter, such an IQ signal based on the reflected wave signal derived from the plane wave transmitted in the direction of the deflection angle of 10° is referred to as a "third IQ signal". Note that, since the plane wave is continuously transmitted twice in the direction of the deflection angle of 10°, the IQ signal based on the reflected wave signal derived from the plane wave transmitted for the first time is denoted as "third IQ signal (1)", and the IQ signal based on the reflected wave signal derived from the plane wave transmitted for the second time is denoted as "third IQ signal (2)".

As illustrated in FIG. 5B, the beamformer 120 is connected to the plurality of reception circuits 112, the B-mode processing circuit 130, and the MTI filter processing function 141. Then, the IQ signal transmitted from each of the plurality of reception circuits 112 is input to the beamformer 120.

The beamformer 120 performs beamforming on the plurality of IQ signals transmitted by the plurality of reception circuits 112. For example, the beamformer 120 generates reflected wave data (reception signal) 20a illustrated in FIG. 6 by performing pixel beamforming on the plurality of first IQ signals (1), and transmits the reflected wave data 20a to the B-mode processing circuit 130 and the Doppler processing circuit 140.

Here, an example of pixel beamforming will be described. For example, when plane waves are transmitted in multiple directions and coherent compound is performed, it is necessary to obtain signals after beamforming at the same point for plane wave transmission in all directions. In this case, it is most efficient to obtain the beamforming result at the point of the display position (pixel, picture element). Thus, in the present embodiment, the beamformer 120 performs beamforming on the plurality of first IQ signals (1) so that the plurality of signals at the same pixel position in the plurality of pieces of image data for display based on the plurality of first IQ signals (1) is added. That is, the beamformer 120 beamforms the plurality of first IQ signals (1) so that the signals at the same display position are added. Thus, the reflected wave data 20a is generated.

Similarly, the beamformer 120 performs pixel beamforming on the plurality of first IQ signals (2), the plurality of second IQ signals (1), the plurality of second IQ signals (2), the plurality of third IQ signals (1), and the plurality of third IQ signals (2).

Reflected wave data 20b is generated by performing pixel beamforming on the plurality of first IQ signals (2). Reflected wave data 21a is generated by performing pixel beamforming on the plurality of second IQ signals (1). Further, reflected wave data 21b is generated by performing pixel beamforming on the plurality of second IQ signals (2). Reflected wave data 22a is generated by performing pixel beamforming on the plurality of third IQ signals (1). Further, reflected wave data 22b is generated by performing pixel beamforming on the plurality of third IQ signals (2).

Then, as illustrated in (a) of FIG. 6, the beamformer 120 transmits the reflected wave data 20a, the reflected wave data 20b, the reflected wave data 21a, the reflected wave data 21b, the reflected wave data 22a, and the reflected wave data 22b to the B-mode processing circuit 130 and the Doppler processing circuit 140.

As illustrated in FIG. 5B, the B-mode processing circuit 130 is connected to the beamformer 120 and the image generation circuit 150. Then, respective pieces of reflected wave data of the reflected wave data 20a, the reflected wave data 20b, the reflected wave data 21a, the reflected wave data 21b, the reflected wave data 22a, and the reflected wave data 22b transmitted from the beamformer 120 are input to the B-mode processing circuit 130.

The B-mode processing circuit 130 generates the B-mode data on the basis of respective pieces of reflected wave data of the reflected wave data 20a, the reflected wave data 20b, the reflected wave data 21a, the reflected wave data 21b, the reflected wave data 22a, and the reflected wave data 22b. Then, the B-mode processing circuit 130 transmits the generated B-mode data to the image generation circuit 150.

As illustrated in FIG. 5B, the image generation circuit 150 is connected to the B-mode processing circuit 130 and the control circuit 180. Then, the B-mode data transmitted from the B-mode processing circuit 130 is input to the image generation circuit 150.

The image generation circuit 150 generates the B-mode image data on the basis of the B-mode data. Then, the image generation circuit 150 transmits the generated B-mode image data to the control circuit 180.

As illustrated in FIG. 5B, the MTI filter processing function 141 of the Doppler processing circuit 140 is connected to the beamformer 120, the second coherent compound processing function 143, and the autocorrelation signal calculation function 144. Then, respective pieces of reflected wave data of the reflected wave data 20a, the reflected wave data 20b, the reflected wave data 21a, the reflected wave data 21b, the reflected wave data 22a, and the reflected wave data 22b transmitted from the beamformer 120 are input to the MTI filter processing function 141.

The MTI filter processing function 141 applies the MTI filter to the input unequal interval data sequence to obtain an output of the same unequal interval data sequence as the input. For example, the MTI filter processing function 141 applies the MTI filter to an unequal interval data sequence including a plurality of pieces of reflected wave data 20a and a plurality of pieces of reflected wave data 20b illustrated in (b) of FIG. 6. Thus, the MTI filter processing function 141 (MTI filter) outputs a blood flow signal 20c corresponding to the reflected wave data 20a to the second coherent compound processing function 143 and the autocorrelation signal calculation function 144, and outputs a blood flow signal 20d corresponding to the reflected wave data 20b to the second coherent compound processing function 143 and the autocorrelation signal calculation function 144. Note that, in the first embodiment, since the MTI filter processing function 141 applies the MTI filter for each pixel (pixel), the MTI filter is applied by the number of pixels. In addition, the MTI filter processing function 141 applies the MTI filter to an unequal interval data sequence for each direction in which the plane wave is transmitted. In addition, the MTI filter processing function 141 applies the MTI filter to an unequal interval data sequence including unequal interval signals obtained as a result of beamforming by the beamformer 120.

Here, the "unequal interval data sequence" refers to, for example, a data sequence including a plurality of pieces of reflected wave data having different intervals in terms of time obtained by transmitting an ultrasonic wave and receiving a reflected wave with a transmission interval not being constant. Note that the "equal interval data sequence" refers to, for example, a data sequence including reflected wave data at equal intervals in time obtained by transmitting ultrasonic waves at constant transmission intervals and receiving reflected waves. In addition, as a method of applying the MTI filter to an unequal interval data sequence, for example, a known method described in Japanese Patent Application Laid-open No. 2005-176997 or Japanese Patent Application Laid-open No. 2016-2379 is used. Details of a method of applying the MTI filter to the unequal interval data sequence will be described later.

Here, an example of the unequal interval data sequence subjected to the MTI filter will be described. For example, the unequal interval data sequence may include three pieces of reflected wave data 20a and three pieces of reflected wave data 20b. In such a case, the interval between the reflected wave data 20a and the reflected wave data 20b adjacent on the time axis is "T" or "5T", and is not constant.

Similarly, the MTI filter processing function 141 applies the MTI filter to an unequal interval data sequence including a plurality of pieces of reflected wave data 21a and a plurality of pieces of reflected wave data 21b illustrated in (c) of FIG. 6. Thus, the MTI filter processing function 141 (MTI filter) outputs a blood flow signal 21c corresponding to the reflected wave data 21a to the second coherent compound processing function 143 and the autocorrelation signal calculation function 144, and outputs a blood flow signal 21d corresponding to the reflected wave data 21b to the second coherent compound processing function 143 and the autocorrelation signal calculation function 144.

Further, similarly, the MTI filter processing function 141 applies the MTI filter to an unequal interval data sequence including a plurality of pieces of the reflected wave data 22a and a plurality of pieces of the reflected wave data 22b illustrated in (d) of FIG. 6. Thus, the MTI filter processing function 141 (MTI filter) outputs a blood flow signal 22c corresponding to the reflected wave data 22a to the second coherent compound processing function 143 and the autocorrelation signal calculation function 144, and outputs a blood flow signal 22d corresponding to the reflected wave data 22b to the second coherent compound processing function 143 and the autocorrelation signal calculation function 144.

As described above, the MTI filter processing function 141 performs processing of applying the MTI filter to the unequal interval data sequence in the same direction obtained by scanning by the ultrasonic probe 101 and extracting a blood flow signal in each of a plurality of directions. The MTI filter processing function 141 repeats such processing. Then, the MTI filter processing function 141 outputs the extracted blood flow signal to the second coherent compound processing function 143 and the autocorrelation signal calculation function 144 every time the blood flow signal is extracted.

As illustrated in FIG. 5B, the second coherent compound processing function 143 is connected to the MTI filter processing function 141 and the power estimation function 145. Then, the respective blood flow signals of the blood flow signal 20c, the blood flow signal 20d, the blood flow signal 21c, the blood flow signal 21d, the blood flow signal 22c, and the blood flow signal 22d output from the MTI filter processing function 141 are input to the second coherent compound processing function 143.

Then, as illustrated in (e) of FIG. 6, the second coherent compound processing function 143 performs multidirectional plane wave transmission coherent compound by performing complex addition of the blood flow signal 20c, the blood flow signal 20d, the blood flow signal 21c, the blood flow signal 21d, the blood flow signal 22c, and the blood flow signal 22d. That is, the second coherent compound processing function 143 performs complex addition of $A*E=3*2=6$ blood flow signals. In this manner, the second coherent compound processing function 143 generates the addition signal (complex signal) 23 by performing the multidirectional plane wave transmission coherent compound.

Then, the MTI filter processing function 141 and the second coherent compound processing function 143 repeatedly generate the addition signal 23 by repeatedly performing the above-described processing. As described above, the second coherent compound processing function 143 generates a signal by performing complex addition of a plurality of blood flow signals extracted in a plurality of directions.

Then, every time the addition signal 23 is generated, the second coherent compound processing function 143 transmits the generated addition signal 23 to the power estimation function 145.

As illustrated in FIG. 5B, the power estimation function 145 is connected to the second coherent compound processing function 143 and the control circuit 180. Then, the addition signal 23 transmitted from the second coherent compound processing function 143 is input to the power estimation function 145.

Then, the power estimation function 145 estimates the power value by calculating the square of amplitude of the addition signal 23 as the power value of blood flow. For example, the power estimation function 145 estimates the power value from the generated addition signal 23 every time the addition signal 23 is generated. In this manner, the power estimation function 145 estimates the power value of blood flow on the basis of the signal generated by the second coherent compound processing function 143.

Then, the power estimation function 145 transmits the estimated power value to the control circuit 180 every time the power value is estimated.

Next, an example of processing in which the ultrasonic diagnostic apparatus 10 estimates the velocity value of blood flow will be described with reference to FIGS. 5B and 7. As illustrated in FIG. 5B, the autocorrelation signal calculation function 144 is connected to the MTI filter processing function 141 and the first coherent compound processing function 142. Then, the autocorrelation signal calculation function 144 receives the respective blood flow signals of the blood flow signal 20c, the blood flow signal 20d, the blood flow signal 21c, the blood flow signal 21d, the blood flow signal 22c, and the blood flow signal 22d output from the MTI filter processing function 141.

Then, the autocorrelation signal calculation function 144 performs the autocorrelation operation of a lag 1 among E (in this case, E=2) blood flow signals in the same direction. That is, the autocorrelation signal calculation function 144 calculates (generates) the autocorrelation signals (autocorrelation values) of (E−1) lags 1 for each same direction. Here, the autocorrelation signal calculation function 144 calculates the autocorrelation signal of the lag 1 between the two blood flow signals having the shortest interval in the same direction. For example, as illustrated in (a) and (b) of FIG. 7, the autocorrelation signal calculation function 144 calculates an autocorrelation signal 25 of the lag 1 between the blood flow signal 20c and the blood flow signal 20d. Similarly, as illustrated in (a) and (c) of FIG. 7, the autocorrelation signal calculation function 144 calculates an autocorrelation signal 26 of the lag 1 between the blood flow signal 21c and the blood flow signal 21d. Further, as illustrated in (a) and (d) of FIG. 7, the autocorrelation signal calculation function 144 calculates an autocorrelation signal 27 of the lag 1 between the blood flow signal 22c and the blood flow signal 22d. That is, the autocorrelation signal calculation function 144 performs processing of generating an autocorrelation signal by performing the autocorrelation operation on a plurality of blood flow signals in the same direction for each direction.

Then, the autocorrelation signal calculation function 144 repeatedly calculates the autocorrelation signal 25, the autocorrelation signal 26, and the autocorrelation signal 27 by repeatedly performing the above-described processing. Then, the autocorrelation signal calculation function 144 transmits the calculated autocorrelation signal 25, the autocorrelation signal 26, and the autocorrelation signal 27 to the first coherent compound processing function 142 every time the autocorrelation signal 25, the autocorrelation signal 26, and the autocorrelation signal 27 are calculated.

As illustrated in FIG. 5B, the first coherent compound processing function 142 is connected to the autocorrelation signal calculation function 144 and the velocity estimation function 146. Then, each autocorrelation signal of the autocorrelation signal 25, the autocorrelation signal 26, and the autocorrelation signal 27 transmitted from the autocorrelation signal calculation function 144 is input to the first coherent compound processing function 142.

Then, as illustrated in (e) and (f) of FIG. 7, the first coherent compound processing function 142 generates an addition signal (complex signal) 28 by performing complex addition of three signals of the autocorrelation signal 25, the autocorrelation signal 26, and the autocorrelation signal 27. Thus, the first coherent compound processing function 142 by performing complex addition of A*(E−1)=3*1=3 autocorrelation signals. In this manner, the first coherent compound processing function 142 generates the addition signal 28 by performing complex addition of the newly generated autocorrelation signal 25 and autocorrelation signal 26 every time the autocorrelation signal 26, the autocorrelation signal 27, and the autocorrelation signal 27 are newly generated. Thus, the first coherent compound processing function 142 repeatedly generates the addition signal 28.

Then, the first coherent compound processing function 142 transmits the generated addition signal 28 to the velocity estimation function 146 every time the addition signal 28 is generated.

As illustrated in FIG. 5B, the velocity estimation function 146 is connected to the first coherent compound processing function 142 and the control circuit 180. Then, the addition signal 28 transmitted from the first coherent compound processing function 142 is input to the velocity estimation function 146.

The velocity estimation function 146 estimates the velocity value of blood flow by calculating a deflection angle from the addition signal 28 to calculate the velocity value normalized from −π to π. For example, the velocity estimation function 146 estimates the velocity value from the generated addition signal 28 every time the addition signal 28 is generated. That is, the velocity estimation function 146 estimates the velocity value of blood flow on the basis of a complex signal generated by performing complex addition of a plurality of autocorrelation signals generated in a plurality of directions.

Then, the velocity estimation function 146 transmits the estimated velocity value to the control circuit 180 every time the velocity value is estimated.

As illustrated in FIG. 5B, the control circuit 180 is connected to the image generation circuit 150, the power estimation function 145, the velocity estimation function 146, and the display 103. Then, the B-mode image data transmitted from the image generation circuit 150, the power value transmitted from the power estimation function 145, and the velocity value transmitted from the velocity estimation function 146 are input to the control circuit 180.

The control circuit 180 controls the display 103 so as to display the B-mode image based on the B-mode image data, and the power value of blood flow and the velocity value of blood flow on the display 103. Here, when displaying the velocity value of blood flow, the control circuit 180 controls the display 103 to display the velocity value of blood flow only at a place where the power value of blood flow is equal to or more than a certain value. The azimuth resolution of the velocity value of blood flow is not improved by complex addition in different transmission directions, but the azimuth resolution of the power value of blood flow is improved by complex addition in different transmission directions. Thus, by displaying the velocity value only at a place where the power value of blood flow is equal to or more than a certain value, it is possible to suppress the velocity value of blood flow from being displayed on an artifact portion such as a side lobe.

In the processing illustrated in FIG. 7, since the phase information is changed to the movement amount by autocorrelation as compared with (e) and (f) of FIG. 6, the phase information of the period T (1/PRF) is averaged among the multidirectional plane wave transmissions. In the conventional coherent compound illustrated in FIG. 1, only motion information of the period "A*T" can be obtained. On the other hand, according to the first embodiment, the motion information of the period T is obtained. As described above, according to the first embodiment, the aliasing velocity is improved by A times as compared with the conventional coherent compound illustrated in FIG. 1. Therefore, according to the first embodiment, it is possible to suppress a decrease in the aliasing velocity when the multidirectional plane wave transmission compound is applied to the color Doppler.

Figure 3:
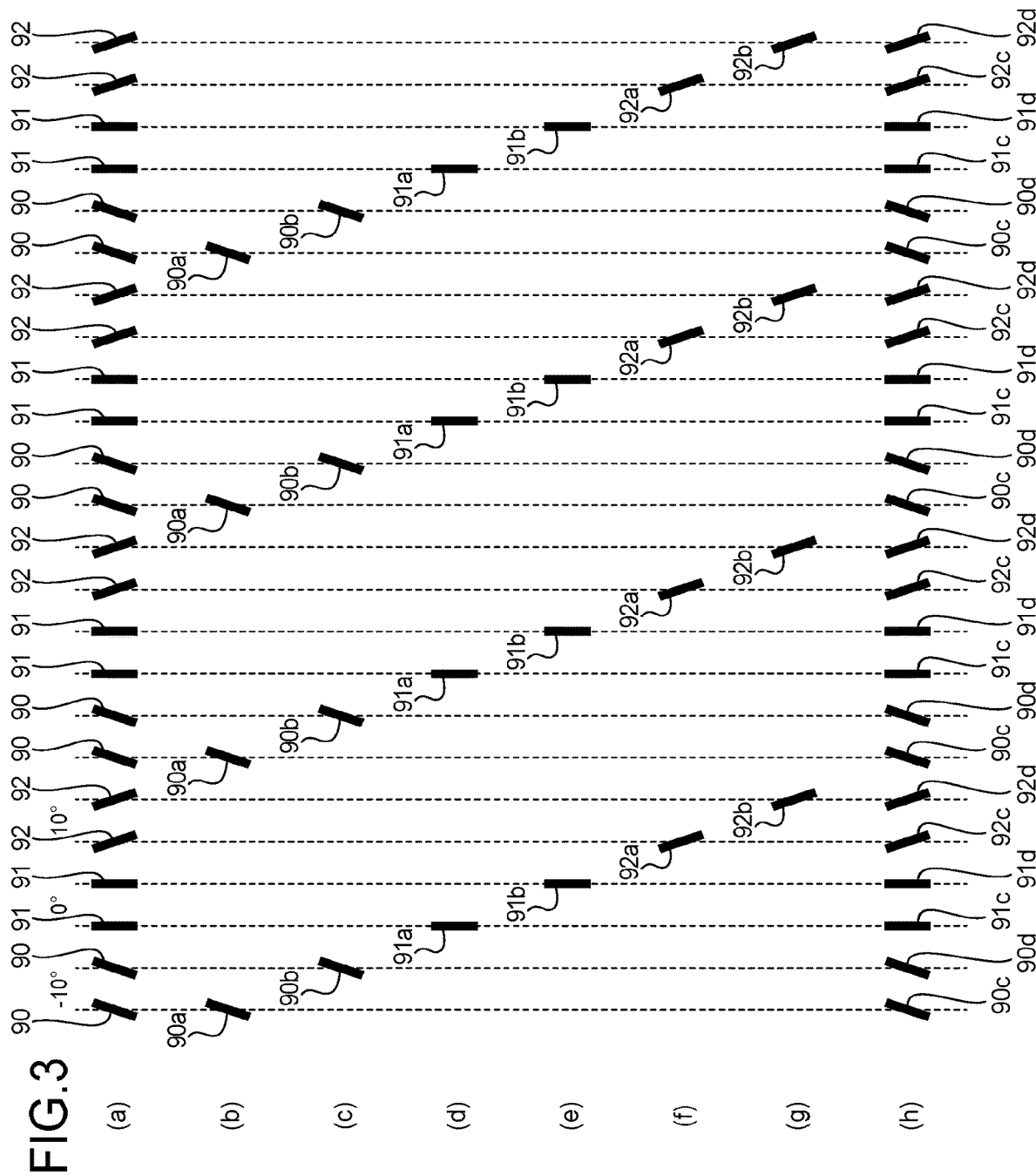
FIG. 3 is a diagram for describing an example of a method of improving aliasing velocity to PRF/2.
Figure 8A:
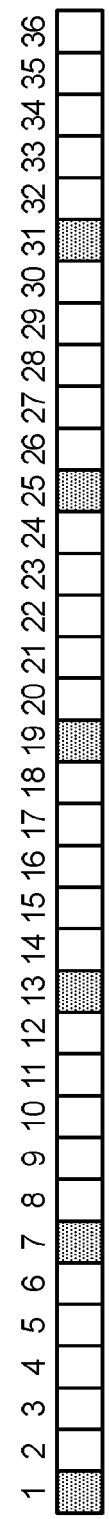
FIG. 8A is a diagram illustrating an equal interval data sequence illustrated in (b) of FIG. 3.
Figure 8B:
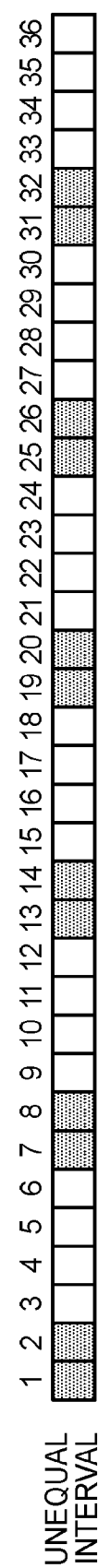
FIG. 8B is a diagram illustrating an unequal interval data sequence illustrated in (b) of FIG. 6.
Figure 8C:
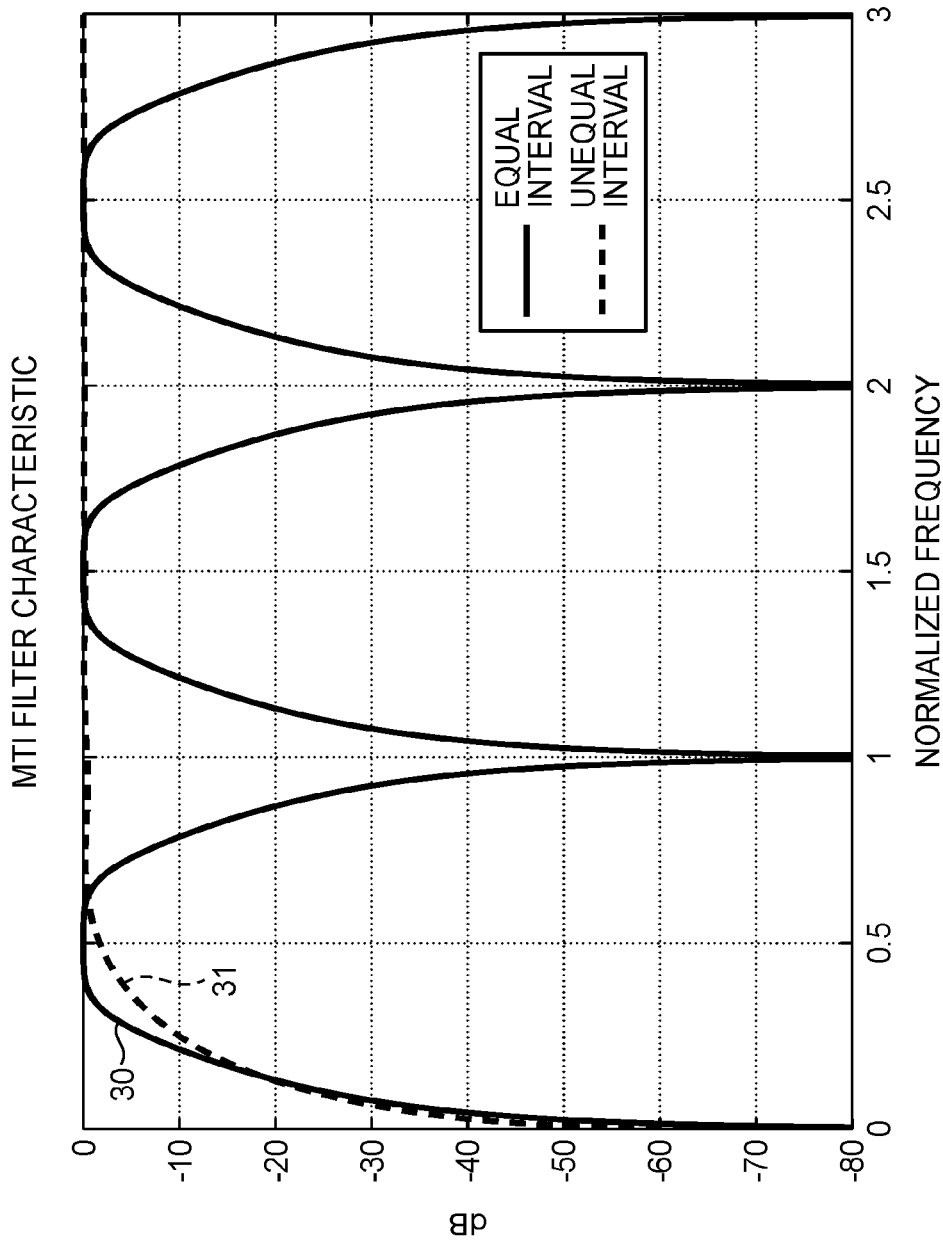
FIG. 8C is a diagram illustrating a characteristic of an MTI filter of a Butterworth IIR type with respect to the equal interval data sequence, and a characteristic of the MTI filter by polynomial fitting using a least squares method with respect to the unequal interval data sequence.

FIG. 8A is a diagram illustrating an equal interval data sequence (a data sequence including the plurality of reception signals 90a) illustrated in part (b) of FIG. 3. FIG. 8B is a diagram illustrating an unequal interval data sequence (a data sequence including a plurality of pieces of reflected wave data 20a and a plurality of pieces of reflected wave data 20b) illustrated in part (b) of FIG. 6. FIG. 8C is a diagram illustrating a characteristic of an MTI filter of a Butterworth IIR type with respect to an equal interval data sequence, and a characteristic of the MTI filter (the MTI filter generated by the method described in Japanese Patent Application Laid-open No. 2005-176997) by polynomial fitting using the least squares method with respect to an unequal interval data sequence. FIG. 8C illustrates a curve 30 indicating the characteristic of the MTI filter of the Butterworth IIR type with respect to the equal interval data sequence, and a curve 31 indicating the characteristic of the MTI filter by the polynomial fitting using the least squares method for the unequal interval data sequence.

Figure 4:
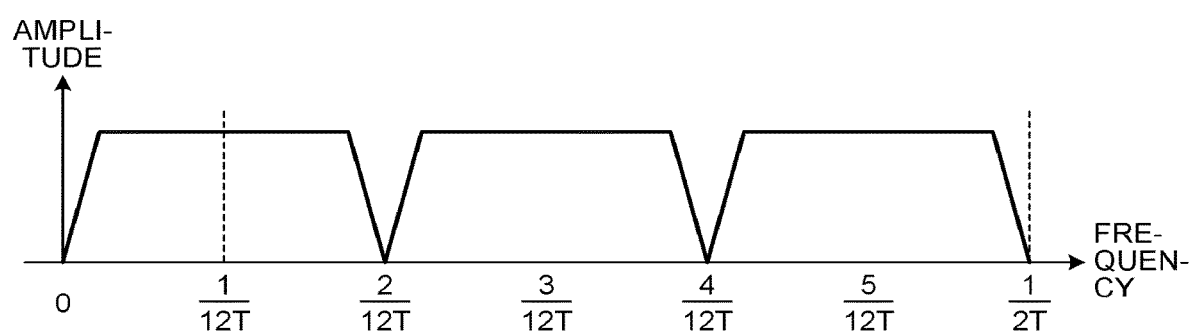
FIG. 4 is a diagram illustrating an example of frequency characteristics of a data sequence including a plurality of blood flow signals arranged in (h) of FIG. 3.

As indicated by the curve 30, a blind frequency occurs in an equal interval data sequence. However, as indicated by the curve 31, in the unequal interval data sequence, no blind frequency occurs, indicating clear high-pass filter characteristics even when the Nyquist frequency 0.5 (position of 1/(12T) in FIG. 4) for the period 6T is exceeded on the normalized frequency axis of the horizontal axis.

In general, in a color Doppler for normal transmission, only about 4 to 16 signals can be used in a data sequence input to the MTI filter. On the other hand, in the multidirectional plane wave transmission of the first embodiment, an infinite number of signals (data) can be used in principle for the data sequence input to the MTI filter. Thus, according to the first embodiment, it is possible to generate the MTI filter having good characteristics even in the unequal interval data sequence.

Here, a method in which the MTI filter processing function 141 generates the MTI filter by polynomial fitting using the least squares method for the unequal interval data sequence on the basis of the method of Japanese Patent Application Laid-open No. 2005-176997 described above will be described. In the method disclosed in Japanese Patent Application Laid-open No. 2005-176997, the unequal interval data sequence is subtracted from the original signal by polynomial fitting using a least squares method. This filter can be calculated in advance as a matrix as illustrated in Expression 6 of Japanese Patent Application Laid-open No. 2005-176997. Since there is a mathematical expression other than the least squares method, the least squares method may be used. A time sequence vector a of the unequal interval data sequence illustrated in FIG. 8B is expressed by the following Expression (1).

$$a=(1\ 2\ 7\ 8\ 13\ 14\ 19\ 20\ 25\ 26\ 31\ 32)^T \quad (1)$$

However, in Expression (1), $[\ ]^T$ represents a transposed matrix. In a case of approximation to a second-order polynomial, the matrix A is defined as illustrated in the following expression (2).

$$A=(a.\hat{\ }0\ a.\hat{\ }1\ a.\hat{\ }2) \quad (2)$$

However, "a.^k (k is an integer)" means that each of a plurality of elements of the time sequence vector a is raised to the power of k. When the number of elements of the time sequence vector a is N (12 in this example), the MTI filter matrix W is expressed by the following Expression (3).

$$W=I-A(A^TA)^{-1}A^T \quad (3)$$

Thus, the MTI filter processing function 141 may generate the MTI filter matrix W using Expressions (1) to (3). Note that the characteristics of the MTI filter approximated up to the first-order polynomial are the characteristics indicated by the curve 31 illustrated in FIG. 8C above.

It seems that the above method does not directly use the least squares method. However, the above method is a solution of a least squares method using a pseudo inverse matrix. Since there is a plurality of methods other than the above-described method for solving the least squares method, any method may be used as long as it is mathematically equivalent to the above-described method.

Next, a method in which the MTI filter processing function 141 generates the MTI filter by a method using principal component analysis on the unequal interval data sequence on the basis of the method described in Japanese Patent Application Laid-open No. 2016-2379 will be described. In the method disclosed in Japanese Patent Application Laid-open No. 2016-2379, fitting is performed with a high-order eigenvalue (main component) of a covariance matrix in a time direction averaged in a two-dimensional space, and subtraction is performed from the original signal. This method is the same as a method called principal component analysis. In Japanese Patent Application Laid-open No. 2016-2379, the filter matrix is expressed as a filter matrix illustrated in Expression 5. The method using singular values is also mathematically equivalent thereto. Since there is a mathematical expression other than this, it may be used.

Let $x_i$ be the input data sequence vector from a spatial location i. Then, the covariance matrix $R_{xx}$ is calculated by the following Expression (4).

$$R_{xx} = \frac{1}{M}\sum_{m=1}^{M} x_m x_m^H \quad (4)$$

In Expression (4), $x_m$ represents a column vector of the reception data at the same position of the transmission data at L different times. In addition, H represents a complex conjugate transposed matrix. Further, m represents a sample point in a space from 1 to M.

A matrix obtained by performing eigenvalue decomposition on $R_{xx}$ and arranging eigenvectors as a column matrix in descending order of the eigenvalues is defined as V. When a matrix S in which P elements are 1 and the rest are zero is created from the top of the diagonal elements in a diagonal matrix of L rows and L columns, $VSV^H$ is a matrix that approximates a signal with a main component. When this is a tissue movement (clutter), a result obtained by subtracting the main component from the original signal can be regarded as a blood flow signal. Therefore, when a matrix in which P elements are zero and the rest are 1 from the top in the diagonal matrix is T, the MTI filter matrix W is expressed by the following Expression (5).

$$W=I-VSV^H=VTV^H \quad (5)$$

Thus, the MTI filter processing function 141 may generate the MTI filter matrix W using Expressions (4) and (5). Note that, although the method of obtaining the eigenvalue and the eigenvector by the eigenvalue decomposition has been described in the above example, a method of performing the principal component analysis from the singular value and the singular vector by singular value decomposition, or another mathematically equivalent method may be used.

FIG. 9 is a flowchart illustrating a flow of an example of processing executed by the ultrasonic diagnostic apparatus 10 according to the first embodiment. The processing illustrated in FIG. 9 is processing of displaying the B-mode image, the power value and the velocity value of blood flow. In addition, the processing illustrated in FIG. 9 is executed every time the ultrasonic probe 101 performs scanning to transmit a plane wave in the A (for example, 3) directions and to continuously transmit a plane wave E (for example, 2) times in each direction.

As illustrated in FIG. 9, the reception circuit 112 generates an IQ signal (reception signal) on the basis of the reflected wave signal derived from the plane wave transmitted in each direction, and transmits the generated IQ signal to the beamformer 120 (step S101). For example, as described above, the reception circuit 112 generates the first IQ signal (1), the first IQ signal (2), the second IQ signal (1), the second IQ signal (2), the third IQ signal (1), and the third IQ signal (2).

Then, the beamformer 120 performs pixel beamforming on the plurality of IQ signals transmitted by the plurality of reception circuits 112, and transmits reflected wave data generated by the pixel beamforming to the B-mode processing circuit 130 and the MTI filter processing function 141 (step S102). For example, in step S102, the beamformer 120 generates the reflected wave data 20*a*, the reflected wave data 20*b*, the reflected wave data 21*a*, the reflected wave data 21*b*, the reflected wave data 22*a*, and the reflected wave data 22*b*. Then, the beamformer 120 transmits the reflected wave data to the B-mode processing circuit 130 and the MTI filter processing function 141.

The B-mode processing circuit 130 and the image generation circuit 150 generate the B-mode image data on the basis of the reflected wave data transmitted from the beamformer 120, and transmit the generated B-mode image data to the control circuit 180 (step S103). Specifically, in step S103, for example, the B-mode processing circuit 130 generates the B-mode data on the basis of respective pieces of reflected wave data of the reflected wave data 20*a*, the reflected wave data 20*b*, the reflected wave data 21*a*, the reflected wave data 21*b*, the reflected wave data 22*a*, and the reflected wave data 22*b*. Then, the image generation circuit 150 generates the B-mode image data on the basis of the generated B-mode data.

In addition, the MTI filter processing function 141 extracts a blood flow signal by applying the MTI filter to the unequal interval data sequence for each direction in which the plane wave is transmitted, and outputs the extracted blood flow signal to the second coherent compound processing function 143 and the autocorrelation signal calculation function 144 (step S104). In step S104, for example, as described above, the blood flow signal 20*c*, the blood flow signal 20*d*, the blood flow signal 21*c*, the blood flow signal 21*d*, the blood flow signal 22*c*, and the blood flow signal 22*d* are output from the MTI filter.

Then, the second coherent compound processing function 143 performs the multidirectional plane wave transmission coherent compound by performing complex addition of the blood flow signal 20*c*, the blood flow signal 20*d*, the blood flow signal 21*c*, the blood flow signal 21*d*, the blood flow signal 22*c*, and the blood flow signal 22*d* (step S105). Thus, an addition signal (complex signal) 23 is generated. In step S105, the second coherent compound processing function 143 transmits the generated addition signal 23 to the power estimation function 145.

Then, the power estimation function 145 estimates the power value of blood flow by calculating the square of the amplitude of the addition signal 23 as the power value of blood flow, and transmits the estimated power value to the control circuit 180 (step S106).

Furthermore, the autocorrelation signal calculation function 144 calculates autocorrelation signals of (E−1) lags 1 for each same direction, and transmits the calculated autocorrelation signals to the first coherent compound processing function 142 (step S107). For example, in step S107, the autocorrelation signal 25, the autocorrelation signal 26, and the autocorrelation signal 27 are calculated.

Then, the first coherent compound processing function 142 generates the addition signal 28 by performing complex addition of the three signals of the autocorrelation signal 25, the autocorrelation signal 26, and the autocorrelation signal 27 (step S108). In step S108, the first coherent compound processing function 142 transmits the generated addition signal 28 to the velocity estimation function 146.

Then, the velocity estimation function 146 estimates the velocity value of blood flow by calculating the deflection angle from the addition signal 28 to calculate the velocity value normalized from $-\pi$ to $\pi$, and transmits the estimated velocity value to the control circuit 180 (step S109).

Then, the control circuit 180 controls the display 103 so as to display the B-mode image based on the B-mode image data and the power value of blood flow and the velocity value of blood flow on the display 103 (step S110), and ends the processing illustrated in FIG. 9.

Figure 10A:
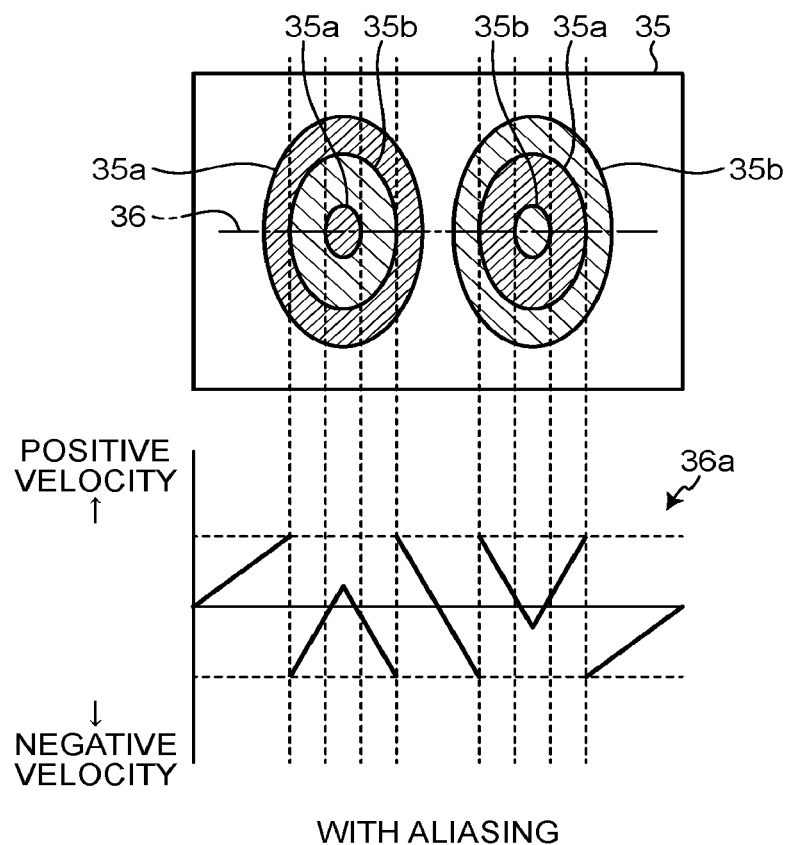
FIG. 10A is a diagram illustrating an example of display on a color Doppler in a case where plane waves are transmitted in three directions and coherent compound is performed as illustrated in FIG. 1.

FIG. 10A is a diagram illustrating an example of display on a color Doppler in a case where plane waves are transmitted in three directions and coherent compound is performed as illustrated in FIG. 1. FIG. 10B is a diagram illustrating an example of display of a color Doppler obtained by the ultrasonic diagnostic apparatus 10 according to the first embodiment.

In FIG. 10A, image 35 illustrates an incoming blood flow 35*a* and a blood flow 35*b* moving away. FIG. 10A illustrates a velocity profile 36*a* on a line segment 36. The positive velocity is the velocity of blood flow 35*a* approaching, and the negative velocity is the velocity of blood flow 35*b* moving away.

In FIG. 10B, an image 37 illustrates the blood flow 35*a* approaching, and the blood flow 35*b* moving away. FIG. 10B illustrates a velocity profile 38*a* on a line segment 38. Again, the positive velocity is the velocity of blood flow 35*a* approaching, and the negative velocity is the velocity of blood flow 35*b* moving away.

In FIG. 10A, the blood flows 85*a* and 85*b* are displayed as double aliasing. On the other hand, in FIG. 10B, the blood flows 85*a* and 85*b* are displayed without aliasing. This is because the aliasing velocity in the first embodiment is three times the aliasing velocity when the plane wave is transmitted in three directions and the coherent compound is performed as illustrated in FIG. 1. As described above, the aliasing velocity is improved by "A" times indicating the number of directions in which the plane wave is transmitted.

The first embodiment has been described above. According to the first embodiment, as described above, it is possible to suppress a decrease in the aliasing velocity when the multidirectional plane wave transmission compound is applied to the color Doppler.

Second Embodiment

Next, an ultrasonic diagnostic apparatus 10*a* according to a second embodiment will be described. In the first embodiment, the MTI filter is applied to the signal after beamforming, whereas in the second embodiment, the MTI filter is applied to the signal from each vibrator 101*a* before beamforming. Hereinafter, in the description of the second embodiment, points different from the first embodiment will be mainly described, and description of configurations similar to those of the first embodiment may be omitted.

Figure 11A:
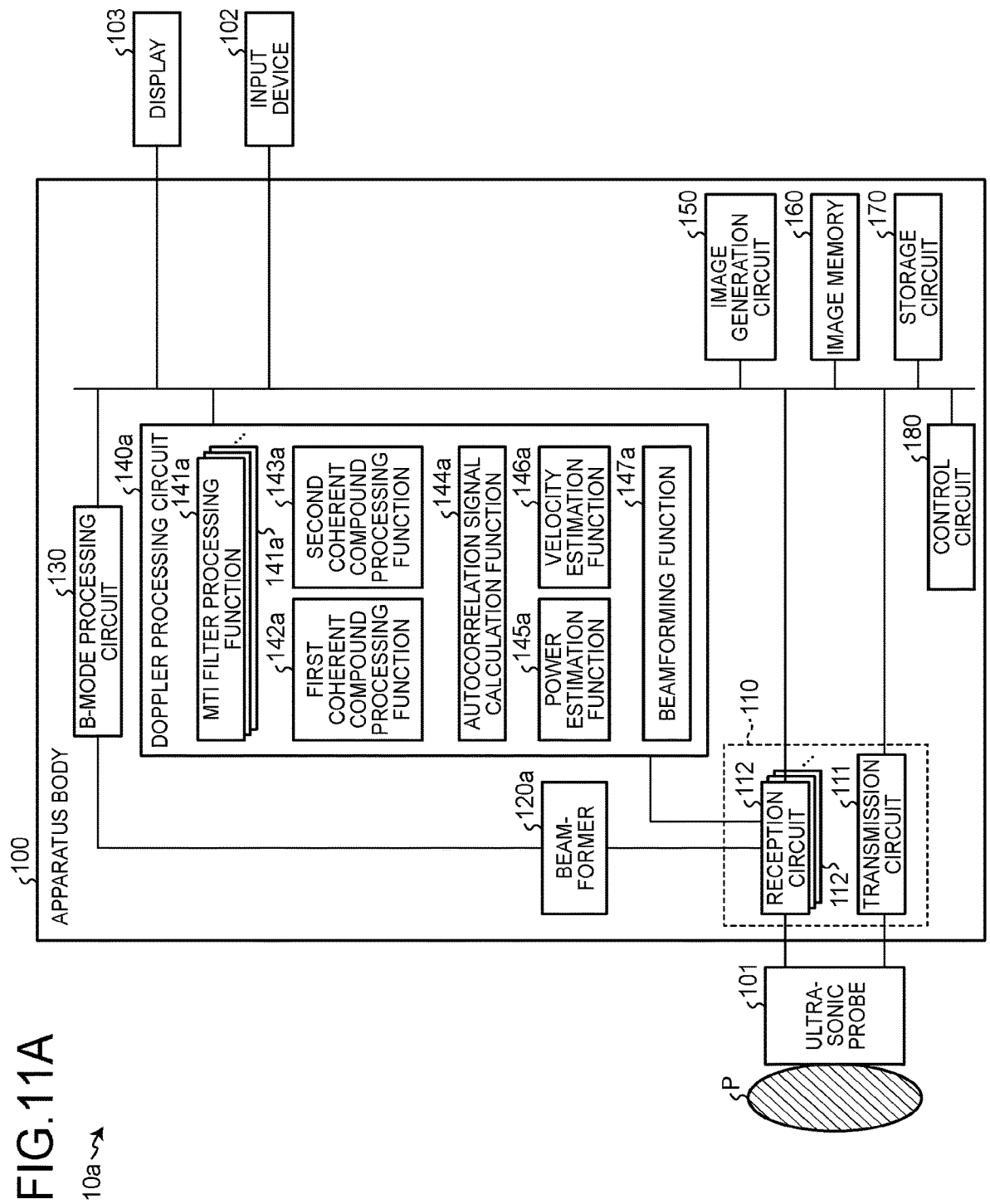
FIG. 11A is a block diagram illustrating a configuration example of an ultrasonic diagnostic apparatus according to a second embodiment.

FIG. 11A is a block diagram illustrating a configuration example of the ultrasonic diagnostic apparatus 10*a* according to the second embodiment. The ultrasonic diagnostic apparatus 10*a* according to the second embodiment is different from the ultrasonic diagnostic apparatus 10 according to the first embodiment in that a beamformer 120*a* and a Doppler processing circuit 140*a* are provided instead of the beamformer 120 and the Doppler processing circuit 140. In addition, a part of the function of the reception circuit 112 according to the second embodiment is different from a part of the function of the reception circuit 112.

In the first embodiment, the case where the reception circuit 112 transmits the IQ signal as a reflected wave signal to the beamformer 120 has been described. On the other hand, in the second embodiment, the reception circuit 112 transmits the IQ signal as a reflected wave signal to the beamformer 120a and the Doppler processing circuit 140a. For example, in the second embodiment, similarly to the first embodiment, the reception circuit 112 generates the first IQ signal (1), the first IQ signal (2), the second IQ signal (1), the second IQ signal (2), the third IQ signal (1), and the third IQ signal (2), and transmits these IQ signals to the beamformer 120a and the Doppler processing circuit 140a.

The beamformer 120a generates reflected wave data by performing beamforming (phasing addition) on a plurality of reflected wave signals transmitted by a plurality of reception circuits 112. Here, in the first embodiment described above, the case where the beamformer 120 transmits the generated reflected wave data to the B-mode processing circuit 130 and the Doppler processing circuit 140 has been described. On the other hand, the beamformer 120a according to the second embodiment transmits the generated reflected wave data to the B-mode processing circuit 130. The beamformer 120a is implemented by, for example, a processor. The beamformer 120a is an example of the beamforming processor.

As illustrated in FIG. 11A, the Doppler processing circuit 140a has a plurality of MTI filter processing functions 141a, a first coherent compound processing function 142a, a second coherent compound processing function 143a, an autocorrelation signal calculation function 144a, a power estimation function 145a, a velocity estimation function 146a, and a beamforming function 147a. Here, the MTI filter processing function 141a is an example of the MTI filter processor. In addition, the first coherent compound processing function 142a and the second coherent compound processing function 143a are examples of the addition unit. Further, the autocorrelation signal calculation function 144a, the power estimation function 145a, and the velocity estimation function 146a are examples of the estimation unit. Furthermore, the beamforming function 147a is an example of the beamforming processor.

Here, for example, the respective processing functions of the plurality of MTI filter processing functions 141a, the first coherent compound processing function 142a, the second coherent compound processing function 143a, the autocorrelation signal calculation function 144a, the power estimation function 145a, the velocity estimation function 146a, and the beamforming function 147a, which are components of the Doppler processing circuit 140a illustrated in FIG. 11A, are recorded in the storage device (for example, the storage circuit 170) of the ultrasonic diagnostic apparatus 10a in the form of a program executable by a computer. The Doppler processing circuit 140a is a processor that implements each function corresponding to each program by reading each program from the storage device and executing each read program. In other words, the Doppler processing circuit 140a in a state of reading each program has each function illustrated in the Doppler processing circuit 140a of FIG. 11A. Processes executed by the respective processing functions of the MTI filter processing function 141a, the first coherent compound processing function 142a, the second coherent compound processing function 143a, the autocorrelation signal calculation function 144a, the power estimation function 145a, the velocity estimation function 146a, and the beamforming function 147a will be described later.

Figure 11B:
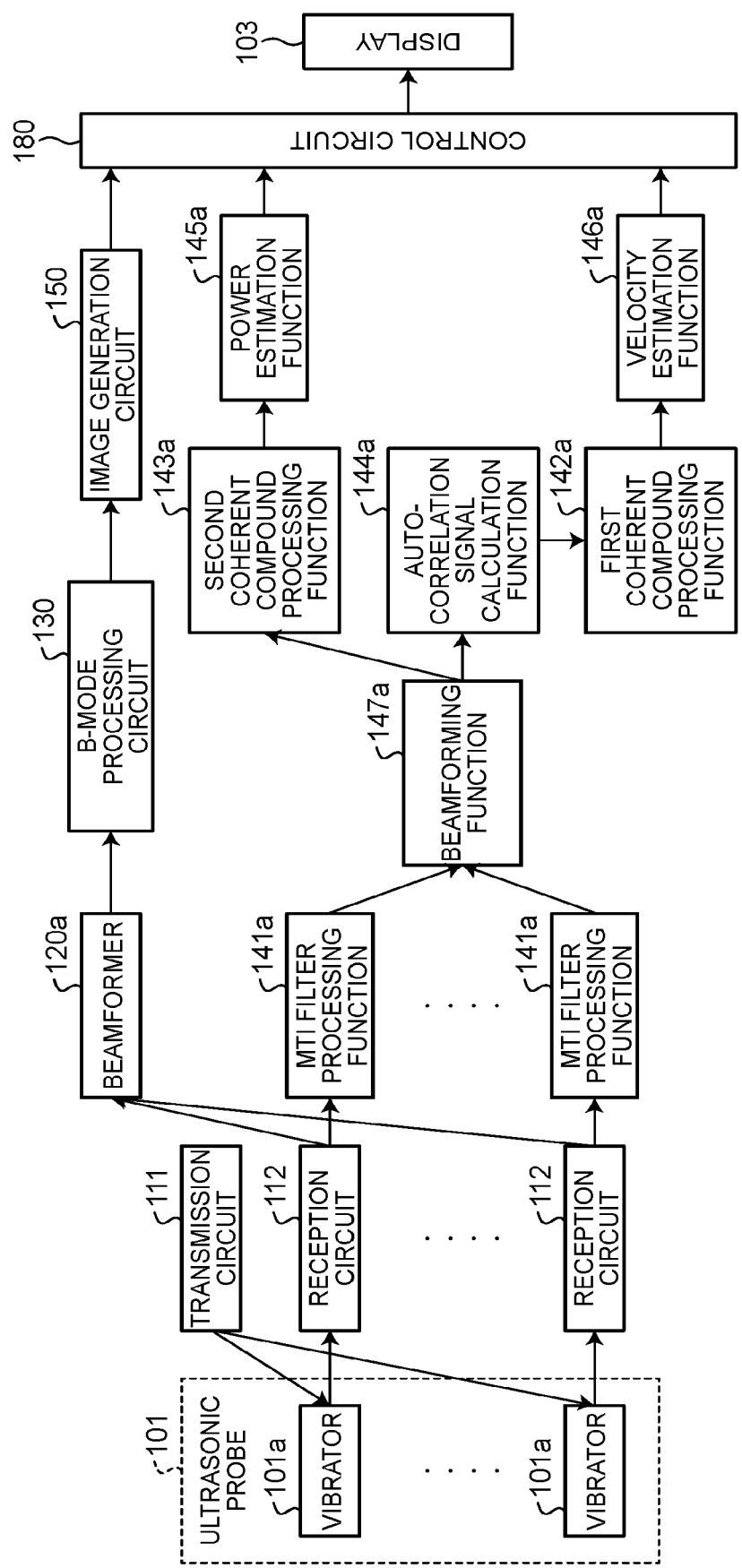
FIG. 11B is a diagram for describing an example of processing executed by the ultrasonic diagnostic apparatus according to the second embodiment.

Next, an example of processing executed by the ultrasonic diagnostic apparatus 10a will be described. FIG. 11B is a diagram for describing an example of processing executed by the ultrasonic diagnostic apparatus 10a according to the second embodiment. More specifically, FIG. 11B is a diagram for describing an example of a flow of various types of information (data, signals, and the like) between respective units (each circuit, each function, and the like) included in the ultrasonic diagnostic apparatus 10a.

As illustrated in FIG. 11B, the beamformer 120a is connected to the plurality of reception circuits 112 and the B-mode processing circuit 130. A plurality of IQ signals is input to the beamformer 120a as a plurality of reflected wave signals. As described above, the beamformer 120a generates reflected wave data by performing beamforming on the plurality of reflected wave signals transmitted by the plurality of reception circuits 112. Then, the beamformer 120a transmits the generated reflected wave data to the B-mode processing circuit 130.

As illustrated in FIG. 11B, the B-mode processing circuit 130 is connected to the beamformer 120a and the image generation circuit 150. Then, the reflected wave data transmitted from the beamformer 120a is input to the B-mode processing circuit 130.

The B-mode processing circuit 130 generates the B-mode data on the basis of the reflected wave data. Then, the B-mode processing circuit 130 transmits the generated B-mode data to the image generation circuit 150.

The image generation circuit 150 according to the second embodiment is connected to the B-mode processing circuit 130 and the control circuit 180 similarly to the image generation circuit 150 according to the first embodiment, and has a similar function to that of the image generation circuit 150 according to the first embodiment.

As illustrated in FIG. 11B, in the second embodiment, one MTI filter processing function 141a is provided corresponding to one channel. Here, one channel corresponds to one vibrator 101a and one reception circuit 112. Thus, one MTI filter processing function 141a is provided corresponding to one vibrator 101a and one reception circuit 112. Therefore, the Doppler processing circuit 140a includes a plurality of MTI filter processing functions 141a corresponding to each of the plurality of vibrators 101a and each of the plurality of reception circuits 112.

As illustrated in FIG. 11B, one MTI filter processing function 141a is connected to one reception circuit 112. Further, one MTI filter processing function 141a is connected to the beamforming function 147a. Then, an IQ signal transmitted from one reception circuit 112 is input to one MTI filter processing function 141a. This IQ signal is a signal of a plurality of sample points.

In the second embodiment, the MTI filter processing function 141a applies the MTI filter to an unequal interval data sequence configured by a plurality of IQ signals (reception signals) from the vibrator 101a. Note that the plurality of IQ signals constituting the unequal interval data sequence is a plurality of IQ signals arranged in time series.

For example, by a method similar to that the MTI filter processing function 141 according to the first embodiment applies the MTI filter to the unequal interval data sequence as illustrated in FIG. 6 to extract the blood flow signal, the MTI filter processing function 141a according to the second embodiment applies the MTI filter to the unequal interval data sequence including the plurality of reception signals from the vibrator 101a to extract the blood flow signal.

Then, the MTI filter processing function 141a outputs the extracted blood flow signal to the beamforming function 147a. Therefore, the plurality of MTI filter processing functions 141a illustrated in FIG. 11B output the plurality of blood flow signals to the beamforming function 147a.

As illustrated in FIG. 11B, the beamforming function 147a is connected to the plurality of MTI filter processing functions 141a, the second coherent compound processing function 143a, and the autocorrelation signal calculation function 144a. Then, the plurality of blood flow signals transmitted from the plurality of MTI filter processing functions 141a is input to the beamforming function 147a.

Then, the beamforming function 147a performs pixel beamforming on a plurality of blood flow signals. For example, the beamforming function 147a performs the pixel beamforming on a plurality of blood flow signals to generate a signal after pixel beamforming by a method similar to the method in which the beamformer 120 according to the first embodiment performs the pixel beamforming on the plurality of IQ signals to generate the reflected wave data. The signal after pixel beamforming is a signal obtained by the pixel beamforming and is also a blood flow signal subjected to the pixel beamforming. Then, the beamforming function 147a transmits the generated signal after pixel beamforming to the second coherent compound processing function 143a and the autocorrelation signal calculation function 144a.

As illustrated in FIG. 11B, the second coherent compound processing function 143a is connected to the beamforming function 147a and the power estimation function 145a. Then, the signal after pixel beamforming transmitted from the beamforming function 147a is input to the second coherent compound processing function 143a.

The second coherent compound processing function 143a generates an addition signal (complex signal) by performing complex addition of a plurality of signals after pixel beamforming generated in a plurality of directions by a method similar to the method for generating the addition signal 23 by performing complex addition of a plurality of blood flow signals extracted in a plurality of directions by the second coherent compound processing function 143 according to the first embodiment. That is, the second coherent compound processing function 143a performs the multidirectional plane wave transmission coherent compound by performing complex addition of a plurality of signals after pixel beamforming. Then, the second coherent compound processing function 143a transmits the generated addition signal to the power estimation function 145a.

As illustrated in FIG. 11B, the power estimation function 145a is connected to the second coherent compound processing function 143a and the control circuit 180. Then, the addition signal transmitted from the second coherent compound processing function 143a is input to the power estimation function 145a.

Then, the power estimation function 145a estimates the power value of blood flow by a method similar to the method in which the power estimation function 145 according to the first embodiment estimates the power value of blood flow. For example, the power estimation function 145a estimates the power value by calculating the square of the amplitude of the input addition signal as the power value of blood flow. For example, the power estimation function 145a estimates the power value from the generated addition signal every time the addition signal is generated. In this manner, the power estimation function 145a estimates the power value of blood flow on the basis of the signal generated by the second coherent compound processing function 143a.

Then, the power estimation function 145a transmits the estimated power value to the control circuit 180 every time the power value is estimated.

Further, as illustrated in FIG. 11B, the autocorrelation signal calculation function 144a is connected to the beamforming function 147a and the first coherent compound processing function 142a. Then, the signal after pixel beamforming transmitted from the beamforming function 147a is input to the autocorrelation signal calculation function 144a.

The autocorrelation signal calculation function 144a performs the autocorrelation operation of the lag 1 between the E signals after pixel beamforming in the same direction by a method similar to the method in which the autocorrelation signal calculation function 144 according to the first embodiment performs the autocorrelation operation of the lag 1 between the E blood flow signals in the same direction. That is, the autocorrelation signal calculation function 144a calculates the autocorrelation signals of the (E−1) lags 1 for each same direction. As described above, the autocorrelation signal calculation function 144a performs, for each direction, the processing of generating an autocorrelation signal by performing the autocorrelation operation on a plurality of signals after beamforming in the same direction.

Then, the autocorrelation signal calculation function 144a transmits the generated autocorrelation signal to the first coherent compound processing function 142a every time the autocorrelation signal is generated.

As illustrated in FIG. 11B, the first coherent compound processing function 142a is connected to the autocorrelation signal calculation function 144a and the velocity estimation function 146a. Then, the autocorrelation signal transmitted from the autocorrelation signal calculation function 144a is input to the first coherent compound processing function 142a.

Then, the first coherent compound processing function 142a performs complex addition of the input (A*(E−1)) autocorrelation signals by a method similar to the method in which the first coherent compound processing function 142 according to the first embodiment performs complex addition of the (A*(E−1)) autocorrelation signals. In this manner, the first coherent compound processing function 142a generates the addition signal by performing complex addition of the input (A*(E−1)) autocorrelation signals.

Then, the first coherent compound processing function 142a transmits the generated addition signal to the velocity estimation function 146a every time the addition signal is generated.

As illustrated in FIG. 11B, the velocity estimation function 146a is connected to the first coherent compound processing function 142a and the control circuit 180. Then, the addition signal transmitted from the first coherent compound processing function 142a is input to the velocity estimation function 146a.

Then, the velocity estimation function 146a estimates the velocity value of blood flow by a method similar to the method in which the velocity estimation function 146 according to the first embodiment estimates the velocity value of blood flow. For example, the velocity estimation function 146a estimates the velocity value of blood flow by calculating the deflection angle from the input addition signal to calculate the velocity value normalized from $-\pi$ to $\pi$. For example, the velocity estimation function 146a estimates the velocity value from the generated addition signal every time the addition signal is generated. Thus, the velocity estimation function 146a estimates the velocity value of blood flow on the basis of the signal generated by the first coherent compound processing function 142a.

Then, the velocity estimation function 146a transmits the estimated velocity value to the control circuit 180 every time the velocity value is estimated.

The control circuit 180 according to the second embodiment performs processing similar to the processing executed by the control circuit 180 according to the first embodiment. That is, the control circuit 180 according to the second embodiment controls the display 103 so as to display the B-mode image based on the B-mode image data, and the power value of blood flow and the velocity value of blood flow on the display 103.

Here, in the first embodiment described above, the MTI filter processing function 141 applies the MTI filter by the number of pixels. On the other hand, in the second embodiment, the plurality of MTI filter processing functions 141a apply the MTI filter for (the number of vibrators 101a×the number of sample points). As described above, in the second embodiment, since the MTI filter is applied before the pixel beamforming, the operation amount of the plurality of MTI filter processing functions 141a may be "(the number of elements×the number of sample points)/the number of pixels" times the operation amount of the MTI filter processing function 141.

FIG. 12 is a flowchart illustrating a flow of an example of processing executed by the ultrasonic diagnostic apparatus 10a according to the second embodiment. The process illustrated in FIG. 12 is processing of displaying the B-mode image, the power value and the velocity value of blood flow. In addition, the processing illustrated in FIG. 12 is executed every time the ultrasonic probe 101 performs scanning to transmit a plane wave in the A (for example, 3) directions and to continuously transmit a plane wave E (for example, 2) times in each direction.

As illustrated in FIG. 12, the reception circuit 112 generates an IQ signal (reception signal) on the basis of the reflected wave signal derived from the plane wave transmitted in each direction, and transmits the generated IQ signal to the beamformer 120 and the MTI filter processing function 141a (step S201).

Then, the beamformer 120a performs beamforming on a plurality of IQ signals transmitted by the plurality of reception circuits 112, and transmits reflected wave data generated by the beamforming to the B-mode processing circuit 130 (step S202).

The B-mode processing circuit 130 and the image generation circuit 150 generate B-mode image data on the basis of the reflected wave data transmitted from the beamformer 120a, and transmit the generated B-mode image data to the control circuit 180 (step S203). Specifically, in step S203, for example, the B-mode processing circuit 130 generates B-mode data on the basis of the reflected wave data. Then, the image generation circuit 150 generates B-mode image data on the basis of the generated B-mode data, and transmits the generated B-mode image data to the control circuit 180.

Further, in the MTI filter processing function 141, the MTI filter processing function 141a extracts a blood flow signal by applying the MTI filter to an unequal interval data sequence including a plurality of reception signals from the vibrator 101a, and outputs the extracted blood flow signal to the beamforming function 147a (step S204).

The beamforming function 147a performs pixel beamforming on a plurality of blood flow signals to generate a signal after pixel beamforming (step S205). In step S205, the beamforming function 147a transmits the generated signal after pixel beamforming to the second coherent compound processing function 143a and the autocorrelation signal calculation function 144a.

Then, the second coherent compound processing function 143a performs the multidirectional plane wave transmission coherent compound by performing complex addition of a plurality of signals after pixel beamforming generated in a plurality of directions (step S206). Thus, an addition signal (complex signal) is generated. In step S206, the second coherent compound processing function 143a transmits the generated addition signal to the power estimation function 145a.

Then, the power estimation function 145a estimates the power value of blood flow by calculating the square of the amplitude of the input addition signal as the power value of blood flow, and transmits the estimated power value to the control circuit 180 (step S207).

Further, the autocorrelation signal calculation function 144a calculates autocorrelation signals of (E−1) lags 1 for each same direction, and transmits the calculated autocorrelation signals to the first coherent compound processing function 142a (step S208).

Then, the first coherent compound processing function 142a generates an addition signal by performing complex addition of the input (A*(E−1)) autocorrelation signals (step S209). In step S209, the first coherent compound processing function 142a transmits the generated addition signal to the velocity estimation function 146a.

Then, the velocity estimation function 146 estimates the velocity value of blood flow by calculating the deflection angle from the input addition signal to calculate the velocity value normalized from −π to π, and transmits the estimated velocity value to the control circuit 180 (step S210).

Then, the control circuit 180 controls the display 103 so as to display the B-mode image based on the B-mode image data and the power value of blood flow and the velocity value of blood flow on the display 103 (step S211), and ends the processing illustrated in FIG. 12.

The second embodiment has been described above. According to the second embodiment, effects similar to those of the first embodiment can be obtained.

Third Embodiment

In the first embodiment and the second embodiment, the case where the ultrasonic diagnostic apparatuses 10 and 10a execute various types of processing has been described, but the image processing apparatus may execute processing similar to various types of processing executed by the ultrasonic diagnostic apparatuses 10 and 10a. Thus, such an embodiment will be described as a third embodiment. Note that, in the description of the third embodiment, points different from the first embodiment and the second embodiment will be mainly described, and description of configurations similar to those of the first embodiment and the second embodiment may be omitted.

Figure 13:
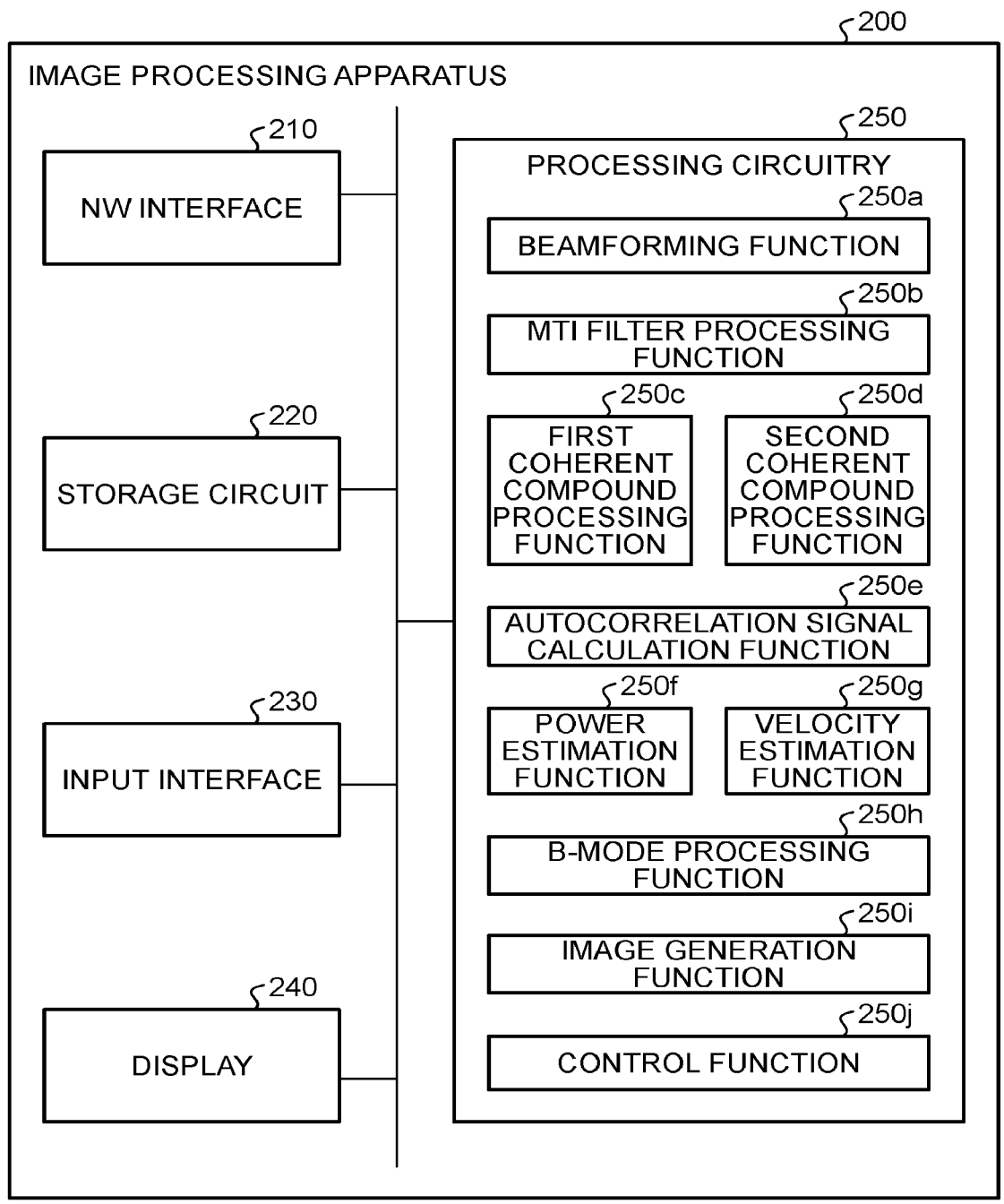
FIG. 13 is a block diagram illustrating a configuration example of an image processing apparatus according to a third embodiment.

FIG. 13 is a diagram illustrating an example of a configuration of an image processing apparatus 200 according to the third embodiment. The image processing apparatus 200 acquires a plurality of reflected wave signal groups (IQ signal groups) from the ultrasonic diagnostic apparatuses 10 and 10a via a network. The reflected wave signal group here is a signal group including the first IQ signal (1), the first IQ signal (2), the second IQ signal (1), the second IQ signal (2), the third IQ signal (1), and the third IQ signal (2) described above. Then, the image processing apparatus 200 executes processing similar to the processing executed by the ultrasonic diagnostic apparatuses 10 and 10a on the plurality of acquired reflected wave signal groups.

As illustrated in FIG. 13, the image processing apparatus 200 includes a network (Network: NW) interface 210, a storage circuit 220, an input interface 230, a display 240, and processing circuitry 250.

The NW interface 210 controls transmission and communication of various types of information and various types of data transmitted and received between the image processing apparatus 200 and the ultrasonic diagnostic apparatuses 10 and 10a. The NW interface 210 is connected to the processing circuitry 250. The NW interface 210 receives a plurality of reflected wave signal groups transmitted by the ultrasonic diagnostic apparatuses 10 and 10a via the network. In this case, the NW interface 210 transmits the plurality of received reflected wave signal groups to the processing circuitry 250. Note that, upon receiving the plurality of reflected wave signal groups, the processing circuitry 250 stores the received plurality of reflected wave signal groups in the storage circuit 220. For example, the NW interface 210 is implemented by a network card, a network adapter, a network interface controller (NIC), or the like.

The storage circuit 220 is connected to the processing circuitry 250 and stores various data. For example, the storage circuit 220 is implemented by a random access memory (RAM), a semiconductor memory element such as a flash memory, a hard disk, or an optical disk. The storage circuit 220 is an example of a storage unit.

Further, the storage circuit 220 stores various types of information used for processing of the processing circuitry 250, processing results by the processing circuitry 250, and the like. For example, the storage circuit 220 stores a plurality of reflected wave signal groups.

The input interface 230 is connected to the processing circuitry 250, converts an input operation received from an operator into an electric signal, and outputs the electric signal to the processing circuitry 250. Note that, in the present specification, the input interface 230 is not limited to one including physical operation components such as a mouse and a keyboard. For example, processing circuit that receives an electric signal corresponding to an input operation from an external input device provided separately from the apparatus and outputs the electric signal to the processing circuitry 250 is also included in examples of the input interface.

For example, the input interface 230 is implemented by a trackball for performing various settings, a switch button, a mouse, a keyboard, a touch pad for performing an input operation by touching an operation surface, a touch screen in which a display screen and the touch pad are integrated, a non-contact input interface using an optical sensor, or a voice input interface.

The display 240 is connected to the processing circuitry 250 and displays various information and various images output from the processing circuitry 250. For example, the display 240 is implemented by a liquid crystal monitor, a cathode ray tube (CRT) monitor, or a touch panel. For example, the display 240 displays a graphical user interface (GUI) for receiving an operator's instruction, various display images, and various processing results by the processing circuitry 250. The display 240 is an example of a display unit.

The processing circuitry 250 is implemented by a processor. The processing circuitry 250 executes a beamforming function 250a, an MTI filter processing function 250b, a first coherent compound processing function 250c, a second coherent compound processing function 250d, an autocorrelation signal calculation function 250e, a power estimation function 250f, a velocity estimation function 250g, a B-mode processing function 250h, an image generation function 250i, and a control function 250j. Here, for example, the respective processing functions of the beamforming function 250a, the MTI filter processing function 250b, the first coherent compound processing function 250c, the second coherent compound processing function 250d, the autocorrelation signal calculation function 250e, the power estimation function 250f, the velocity estimation function 250g, the B-mode processing function 250h, the image generation function 250i, and the control function 250j, which are components of the processing circuitry 250 illustrated in FIG. 13, are recorded in the storage circuit 220 in the form of a program executable by a computer. The processing circuitry 250 reads each program from the storage circuit 220 and executes each read program to implement a function corresponding to each program. In other words, the processing circuitry 250 in a state of reading each program has each function illustrated in the processing circuitry 250 of FIG. 13.

Note that, although FIG. 13 illustrates a case where the respective processing functions of the beamforming function 250a, the MTI filter processing function 250b, the first coherent compound processing function 250c, the second coherent compound processing function 250d, the autocorrelation signal calculation function 250e, the power estimation function 250f, the velocity estimation function 250g, the B-mode processing function 250h, the image generation function 250i, and the control function 250j are implemented by the single processing circuitry 250, the embodiment is not limited thereto. For example, the processing circuitry 250 may be configured by combining a plurality of independent processors, and each processor may implement each processing function by executing each program. In addition, each processing function of the processing circuitry 250 may be implemented by being appropriately distributed or integrated into a single or a plurality of processing circuits.

In the third embodiment, the image processing apparatus 200 performs processing similar to the processing of the first embodiment or the second embodiment on the plurality of reflected wave signal groups stored in the storage circuit 220. Note that, in the third embodiment, when the image processing apparatus 200 executes processing, the storage circuit 220 and the display 240 are used instead of the storage circuit 170 and the display 103 of the first embodiment or the second embodiment.

Specifically, the beamforming function 250a has a function similar to that of the beamformer 120 or the beamforming function 147a. The MTI filter processing function 250b has a function similar to the function of the MTI filter processing function 141 or the MTI filter processing function 141a. However, in a case where the MTI filter processing function 250b has a function similar to the function of the MTI filter processing function 141a, the number of MTI filter processing functions 250b provided in the processing circuitry 250 is the same as the number of MTI filter processing functions 141a.

The first coherent compound processing function 250c has a function similar to the function of the first coherent compound processing function 142 or the first coherent compound processing function 142a. The second coherent compound processing function 250d has a function similar to the function of the second coherent compound processing function 143 or the second coherent compound processing function 143a.

The autocorrelation signal calculation function 250e has a function similar to the function of the autocorrelation signal calculation function 144 or the autocorrelation signal calculation function 144a. The power estimation function 250f has a function similar to the function of the power estimation function 145 or the power estimation function 145a. The velocity estimation function 250g has a function similar to the function of the velocity estimation function 146 or the velocity estimation function 146a.

The B-mode processing function 250h has a function similar to the function of the B-mode processing circuit 130. The image generation function 250i has a function similar to the function of the image generation circuit 150.

The control function 250j has a function similar to the function of the control circuit 180. However, while the control circuit 180 controls the entire ultrasonic diagnostic apparatuses 10 and 10a, the control function 250j controls the entire image processing apparatus 200.

The beamforming function 250a is an example of the beamforming processor. The MTI filter processing function 250b is an example of the MTI filter processor. The first coherent compound processing function 250c and the second coherent compound processing function 250d are examples of the addition unit. The autocorrelation signal calculation function 250e, the power estimation function 250f, and the velocity estimation function 250g are examples of the estimation unit.

The image processing apparatus 200 according to the third embodiment has been described above. According to the third embodiment, effects similar to those of the first embodiment or the second embodiment can be obtained.

Note that, in the first embodiment and the second embodiment described above, the case where the ultrasonic probe 101 transmits a plane wave has been described, but for example, the ultrasonic probe 101 may transmit a diffused wave. Then, the ultrasonic diagnostic apparatuses 10 and 10a may perform processing similar to that of the first embodiment or the second embodiment on the reception signal obtained by transmitting the diffused wave. Similarly, the image processing apparatus 200 may acquire a plurality of reflected wave signal groups obtained by transmitting the diffused wave from the ultrasonic diagnostic apparatuses 10 and 10a. Then, the image processing apparatus 200 may perform processing similar to that of the third embodiment on the plurality of reflected wave signal groups acquired in this manner.

The term "processor" used in the above description means, for example, a circuit such as a central processing unit (CPU), a graphics processing unit (GPU), an application specific integrated circuit (application specific integrated circuit (ASIC), or a programmable logic device (for example, a simple programmable logic device (SPLD), a complex programmable logic device (CPLD), or a field programmable gate array (FPGA)). The processor implements a function by reading and executing a program stored in the storage circuit 170 or the storage circuit 220. Note that, instead of storing the program in the storage circuit 170 or the storage circuit 220, the program may be directly incorporated in the circuit of the processor. In this case, the processor implements a function by reading and executing a program incorporated in the circuit.

Note that the program may be provided by being recorded in a non-transitory computer-readable storage medium such as a compact disk (CD)-ROM, a flexible disk (FD), a recordable (CD-R), or a digital versatile disk (DVD) as a file in a format that can be installed or executed in the computer. In addition, the program may be provided or distributed by being stored on a computer connected to a network such as the Internet and downloaded via the network. For example, this program is configured by a module including each processing function described above. As actual hardware, a processor reads and executes a program from a storage medium such as a ROM, whereby each module is loaded on a main storage device and generated on the main storage device.

According to at least one embodiment described above, it is possible to suppress a decrease in the aliasing velocity when the multidirectional plane wave transmission compound is applied to the color Doppler.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
an ultrasonic probe that repeatedly performs scanning in which a plane wave or a diffused wave is continuously transmitted a plurality of times in a same direction and in a plurality of directions; and
processing circuitry that
repeatedly performs processing of applying, for each of the plurality of directions, a moving target indicator (MTI) filter to an unequal interval data sequence including a plurality of data adjacent on a time axis in the same direction obtained by the scanning, and extracting a blood flow signal in each of the plurality of directions,
repeatedly performs processing of generating an autocorrelation signal by performing an autocorrelation operation on a plurality of blood flow signals in the same direction and for each of the plurality of directions, and
repeatedly estimates a velocity value of blood flow based on a complex signal generated by performing complex addition of a plurality of autocorrelation signals generated for the plurality of directions.

2. The ultrasonic diagnostic apparatus according to claim 1,
wherein the processing circuitry further repeatedly generates a signal by performing complex addition of a plurality of blood flow signals extracted in the plurality of directions, and repeatedly estimates a power value of blood flow based on the generated signal.

3. The ultrasonic diagnostic apparatus according to claim 1, wherein the processing circuitry
further performs beamforming in which signals at a same display position are added to a plurality of reception signals obtained by transmitting the plane wave or the diffused wave, and
applies the MTI filter to the unequal interval data sequence including unequal interval signals, as the plurality of data, obtained as a result of the beamforming.

4. The ultrasonic diagnostic apparatus according to claim 1, wherein the processing circuitry
further extracts a plurality of blood flow signals for a plurality of vibrators by performing, for each of the plurality of vibrators, processing of applying the MTI filter to the unequal interval data sequence including a plurality of reception signals at unequal intervals output from each of the plurality of vibrators included in the ultrasonic probe, and extracts the blood flow signals, further performs beamforming in which signals at a same display position are added to the plurality of blood flow signals, and performs processing of generating the autocorrelation signal by performing the autocorrelation operation on a plurality of signals obtained by the beamforming in the same direction and for each of the plurality directions, and estimates the velocity value of blood flow based on the complex signal generated by performing complex addition of the plurality of autocorrelation signals generated for the plurality of directions.

5. An image processing apparatus, comprising:

processing circuitry that repeatedly performs processing of applying, for each of the plurality of directions, a moving target indicator (MTI) filter to an unequal interval data sequence including a plurality of data adjacent on a time axis in a same direction obtained by repeatedly performs scanning in which a plane wave or a diffused wave is continuously transmitted a plurality of times in the same direction and in the plurality of directions, and extracting a blood flow signal in each of the plurality of directions, repeatedly performs processing of generating an autocorrelation signal by performing an autocorrelation operation on a plurality of blood flow signals in the same direction and for each of the plurality of directions, repeatedly estimates a velocity value of blood flow based on a complex signal generated by performing complex addition of a plurality of autocorrelation signals generated for the plurality of directions, repeatedly generates a signal by performing complex addition of a plurality of blood flow signals extracted in the plurality of directions, and repeatedly estimates a power value of blood flow based on the generated signal.

* * * * *